(12) United States Patent
Discenzo

(10) Patent No.: US 7,104,116 B2
(45) Date of Patent: Sep. 12, 2006

(54) FLUID SENSOR FIXTURE FOR DYNAMIC FLUID TESTING

(75) Inventor: Frederick M. Discenzo, Brecksville, OH (US)

(73) Assignee: Rockwell Automation Technologies, Inc., Mayfield Heights, OH (US)

(*) Notice: Subject to any disclaimer, the term of this patent is extended or adjusted under 35 U.S.C. 154(b) by 13 days.

(21) Appl. No.: 10/670,614

(22) Filed: Sep. 25, 2003

(65) Prior Publication Data

US 2005/0066711 A1 Mar. 31, 2005

(51) Int. Cl.
 *G01N 11/14* (2006.01)
(52) U.S. Cl. .................... 73/54.28; 73/290 R
(58) Field of Classification Search ............. 73/54.28, 73/290 R, 290 V, 290 B, 864.63, 864.64, 73/64.56
See application file for complete search history.

(56) References Cited

U.S. PATENT DOCUMENTS

| | | | |
|---|---|---|---|
| 3,273,394 A * | 9/1966 | Chaney ..................... | 374/157 |
| 3,334,516 A | 8/1967 | Cedrone | |
| 3,421,508 A * | 1/1969 | Nestrock ..................... | 606/21 |
| 3,698,238 A | 10/1972 | Wall et al. | |
| 3,906,795 A * | 9/1975 | Kask ........................ | 73/309 |
| 4,074,717 A * | 2/1978 | Schulze et al. ............... | 606/25 |
| 4,438,203 A | 3/1984 | Wohltjen et al. | |
| 4,742,549 A * | 5/1988 | Roschier ..................... | 382/100 |
| 4,949,070 A | 8/1990 | Wetzel | |
| 5,388,442 A | 2/1995 | Kumar et al. | |
| 5,785,425 A * | 7/1998 | Buchanan ..................... | 374/16 |
| 5,878,813 A * | 3/1999 | Ridgeway, Jr. .............. | 166/162 |
| 6,470,744 B1 * | 10/2002 | Usui et al. ................. | 73/290 R |
| 6,576,193 B1 * | 6/2003 | Cui et al. ..................... | 422/58 |
| 6,644,137 B1 * | 11/2003 | Bellamy et al. ......... | 73/864.63 |
| 6,685,807 B1 * | 2/2004 | Meier .......................... | 204/401 |
| 6,745,626 B1 * | 6/2004 | Usui et al. ................ | 73/290 R |
| 6,771,074 B1 * | 8/2004 | Zou et al. ..................... | 324/446 |
| 6,784,429 B1 * | 8/2004 | De Saro et al. ........ | 250/339.07 |
| 6,792,798 B1 * | 9/2004 | Liang ....................... | 73/152.58 |
| 2004/0173035 A1 * | 9/2004 | Britt ........................ | 73/864.66 |

FOREIGN PATENT DOCUMENTS

DE 19610167 C1 * 2/1997

* cited by examiner

*Primary Examiner*—Hezron Williams
*Assistant Examiner*—Rodney Frank
(74) *Attorney, Agent, or Firm*—Amin & Turocy, LLP; Alexander R. Kuszewski

(57) ABSTRACT

A system that facilitates measurement, analysis, and automatic maintenance of fluid comprises a fluid, and a casing that includes a plurality of apertures is immersed in the fluid. The apertures are opened to permit the fluid to enter the casing and closed to confine a sample of the fluid within the casing. A sensing element within the casing measures at least one parameter of the sample of fluid confined within the casing.

43 Claims, 18 Drawing Sheets

FLUID SENSOR FIXTURE FOR DYNAMIC FLUID TESTING

TECHNICAL FIELD

The present invention generally relates to measurement and analysis of multiple parameters of fluids. More particularly, the invention relates to a system and/or methodology that facilitates real-time in situ measurement and analysis of fluids utilized in machinery, as well as to automatically maintaining fluid in machinery.

BACKGROUND OF THE INVENTION

Dynamoelectric machines such as motors and generators and other rotating machines such as gears and bearing systems are widely employed in industrial and commercial facilities. These machines are relied upon to operate with minimal attention and provide for long, reliable operation. Many facilities operate several hundred or even thousands of such machines concurrently, several of which are integrated into a large interdependent process or system. Several machines, such as aircraft, land vehicles, and marine systems employ micro-electrical mechanical system (MEMs) sensors to obtain measurements related to critical parameters of fluid that operates within the machines. Like most machinery, at least a small percentage of such equipment is prone to failure. Some of these failures can be attributed to loss of lubrication, incorrect lubrication, lubrication breakdown, or lubrication contamination.

Depending on the application, failure of a machine in service can possibly lead to system or process latency, inconvenience, material scrap, machinery damage, hazardous material cleanup, and even a dangerous situation. Thus, it is desirable to diagnose machinery for possible failure or faults early in order to take preventive action and avoid such problems. Absent special monitoring for certain lubrication problems, a problem may have an insidious effect in that although only a minor problem on the outset, the problem could become serious if not detected. For example, bearing problems due to inadequate lubrication, lubrication contamination or other causes may not become apparent until significant damage has occurred.

Proper lubrication facilitates extension of machinery life. For example, when motor lubricant is continuously exposed to high temperatures, high speeds, stress or loads, and an oxidizing environment, the lubricant will deteriorate and lose its lubricating effectiveness. The loss of lubricating effectiveness will affect two main functions of a lubrication system, namely: (1) to reduce friction; and (2) to remove heat. Continued operation of such a degraded system may result in even greater heat generation and accelerated system degradation eventually leading to substantial machinery damage and ultimately catastrophic failure. To protect the motor, the lubricant should be changed in a timely fashion. However, a balance must be struck—on one hand it is undesirable to replace an adequate lubricant but on the other hand it is desired to replace a lubricant that is in its initial stages of breakdown or contamination prior to occurrence of equipment damage. As each particular application of a lubricant is relatively unique with respect to when the lubricant will breakdown or possibly become contaminated, it becomes necessary to monitor the lubricant.

Conventional systems and/or methods for in situ measurement and analysis of fluids in machinery include selectively placing a sensing device in machinery in a position wherein fluid (e.g., lubricating fluid) will flow directly across sensing elements of the sensing device. For example, the sensing device can include sensing elements such as a temperature sensor, a pH sensor, a dielectric sensor, an oxidation-reduction potential sensor, and a viscosity sensor. The sensing device can be utilized to measure various parameters of the lubrication as it flows across such sensing elements, which can be thereafter relayed to a computing system for a detailed analysis of the measurements obtained by the sensing elements. However, measurements obtained by the sensing elements can be compromised via movement of fluid across such sensing elements. Moreover, measuring several desirable parameters requires a particular sample of fluid to remain static for a period of time (e.g., a minute). For example, obtaining measurement of an oxidation level of a fluid requires voltages to be applied to the fluid, thus inducing an oxidation-reduction cycle in the fluid. Constant flow of fluid over the sensing elements, however, inhibits completion of the oxidation-reduction cycle, thus compromising validity of the obtained oxidation measurement. Conventional systems and/or methodologies utilized to obtain measurements of oxidation, and other parameters which need a substantial amount of time for sufficient measurement, require fluid to be extracted from a machine and thereafter tested in a laboratory environment. Such testing results in significant delay in measurement, and can therefore result in delay in lubrication modification and/or replacement if such actions are required. These delays can contribute to accelerated failure of a machine and/or component of a machine.

In various applications, an embedded sensor can be subject to a continuous flow of fluid across sensitive elements designed to obtain measurements relating to a plurality of parameters of a fluid. For instance, flowing fluids can contain metal wear particles that can damage sensing elements or compromise measurements obtained by the embedded sensor. In such applications that an embedded sensor is constantly subject to flowing fluid, a need exists to momentarily expose the sensing elements to the fluid during sensor measurement, and to protect the sensing elements when measurements are not being obtained.

Pertaining to several applications, performance of a sensor is enhanced via altering chemical composition of a fluid to be analyzed. It is not practical, however, to alter chemical composition of a substantial amount of fluid due to cost and possible reduced performance of the fluid. Similarly, sensor performance within several applications can be enhanced via altering temperature of fluid (e.g., altering temperature to particular temperatures or a series of particular temperatures). Heating and/or cooling an entire fluid base, however, is not practical due to energy required for heating and/or cooling the fluid base and potential damaging affects on the fluid and/or structure utilizing the fluid. For these and similar cases, conventional systems require a fluid sample to be extracted from a system and tested within a laboratory environment, wherein chemical composition and/or temperature of the fluid sample can be altered. Such modification and testing is costly and results in significant delay in measurement, and can therefore result in delay in fluid modification and/or replacement if such actions are required.

Measurements relating to machine fluids obtained from sensing elements and/or a laboratory process are then utilized to prevent substantial degradation of the machine fluids, and thus prevent damage to the machine. Even if such measurements are taken at regular intervals, however, a maintenance engineer is still required to effectuate maintenance measures (e.g., fluid addition, fluid replacement, addition of anti-oxidants, . . . ). Particular machinery requiring fluid maintenance can be located at positions on the machinery that is difficult to reach and therefore requires a significant amount of the maintenance engineer's time to perform such maintenance. Furthermore, the maintenance engineer is prone to human error and can add incorrect fluids and/or fluid additives to a particular machine or machine component, as well as provide the machine or machine component with an over-abundance of fluid. These and other similar maintenance errors can result in accelerated failure of the machine and/or machine component.

In view of at least the above, there exists a strong need in the art for a system and/or methodology facilitating improved real-time in situ measurement and analysis of parameters relating to fluid in machinery, and a system and/or methodology for maintaining such fluids.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention facilitates improved real-time in situ measurement, analysis, and automatic maintenance of fluid that is utilized within machinery. Such improvements are accomplished via providing system and/or methodology that obtains a small sample of fluid utilized within machinery and tests and/or alters such sample without requiring lab testing and/or analysis. The sample can be collected via providing a small casing that includes a plurality of apertures that can be automatically opened and closed or manually opened and closed. The casing also includes a multi-element sensor that can obtain measurements of various parameters of a fluid. The casing can be immersed in a fluid flow line or a fluid reservoir, and the apertures can be opened to allow a small portion of fluid to enter the casing and contact sensing elements of the multi-element sensor. The apertures can then be closed, thus confining the sample of fluid within the casing. Such confinement enables accurate measurement of parameters that conventional systems are unable to effectively measure due to a non-static nature of fluid within machinery. For example, prior to conception of the present invention in situ measurement of oxidation levels of a fluid was ineffective due to a significant amount of time required for chemical reactions required for adequate measurement to occur. After the fluid has been confined for a time sufficient to obtain accurate measurements, the apertures can be opened and the fluid can be flushed from the casing. Thereafter, disparate fluid can enter the casing for measurement, analysis, and/or maintenance. Similarly, chemical composition and/or temperature of fluid that has been confined can be altered and/or controlled to facilitate robust sensing analysis. Regularly obtaining samples of fluid from a machine facilitates optimal measurement, analysis, and maintenance of fluid and thereby extends useful life of such fluid. Moreover, the measurements obtained can be employed to predict a time in the future when human intervention for maintaining fluid will be necessary (e.g., a display indicating predicted life of fluid can be employed in connection with the present invention).

Moreover, precise automatic maintenance of fluid within machinery (and thus maintenance of machinery itself) is a result of robust measurement(s) of a variety of fluid parameters. For instance, measurements relating to fluid can be fused via any suitable data fusion techniques and thereafter employed in a control system that maintains fluid (e.g., the control system can maintain volume of fluid within machinery, fluid chemistry, . . . ). Measurement and analysis can also be utilized to direct an alteration in operation or stress on machinery containing the fluid. (e.g., a control system can be provided that utilizes the measured parameters at least in part to control operation of machinery utilizing fluid). For example, if fluid temperature reaches a threshold, the control system can cause a rotating machine to decrease operation speed or decrease load size).

In accordance with one important aspect of the present invention, oxidation levels of fluid within the casing can be reversed, thus elongating useful life of fluid and decreasing probability of human error in maintaining fluid. For example, a three electrode system comprising a working electrode, a counter electrode, and a reference electrode can be provided within a casing to measure oxidation levels as well as reduce oxidation levels in a fluid. A cyclically ramped voltage is applied to the working electrode and the reference electrode, thus generating a current in the counter electrode. Fluid in proximity to the electrodes undergoes an oxidation phase and a reduction phase according to the cyclically ramped voltages. The resulting voltage-current curve can be analyzed to determine an existing amount of oxidation within a sample of fluid. The present invention applies voltages to the electrodes in such a manner to bias the chemical reaction to the reduction phase, thereby reducing oxidation levels within the fluid.

The present invention can also utilize screens in connection with the casing to capture contaminants within a fluid and prevent such contaminants from contacting sensitive sensing elements and/or re-entering a fluid flow line and/or reservoir. Moreover, a flushing mechanism can be provided to flush the contaminants from the screen and remove fluid from the screen. Another advantage of the present invention is an ability to quickly alter conditions of the fluid sample without risking damage to machinery. For instance, a sample of fluid contained by a casing can be quickly heated and/or cooled by an external heating/cooling unit. Such heating and cooling can enable testing of sensing elements within the casing to ensure such sensing elements are operating within design standards. Furthermore, heating a small sample and measuring various parameters of the sample can result in obtainment of valuable predictive data. For example, temperature of fluids tend to increase as speed of rotating machinery increases. As temperature of a fluid typically effects viscosity of the fluid, heating and/or cooling a small sample allows obtainment of more precise measurements of fluid viscosity, additives, and contaminants. Such temperature alteration can also provide predictive data regarding viscosity of a fluid if machine speed is increased.

To the accomplishment of the foregoing and related ends, the invention then, comprises the features hereinafter fully described and particularly pointed out in the claims. The following description and the annexed drawings set forth in detail certain illustrative aspects of the invention. These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

DETAILED DESCRIPTION OF THE INVENTION

Figure 1:
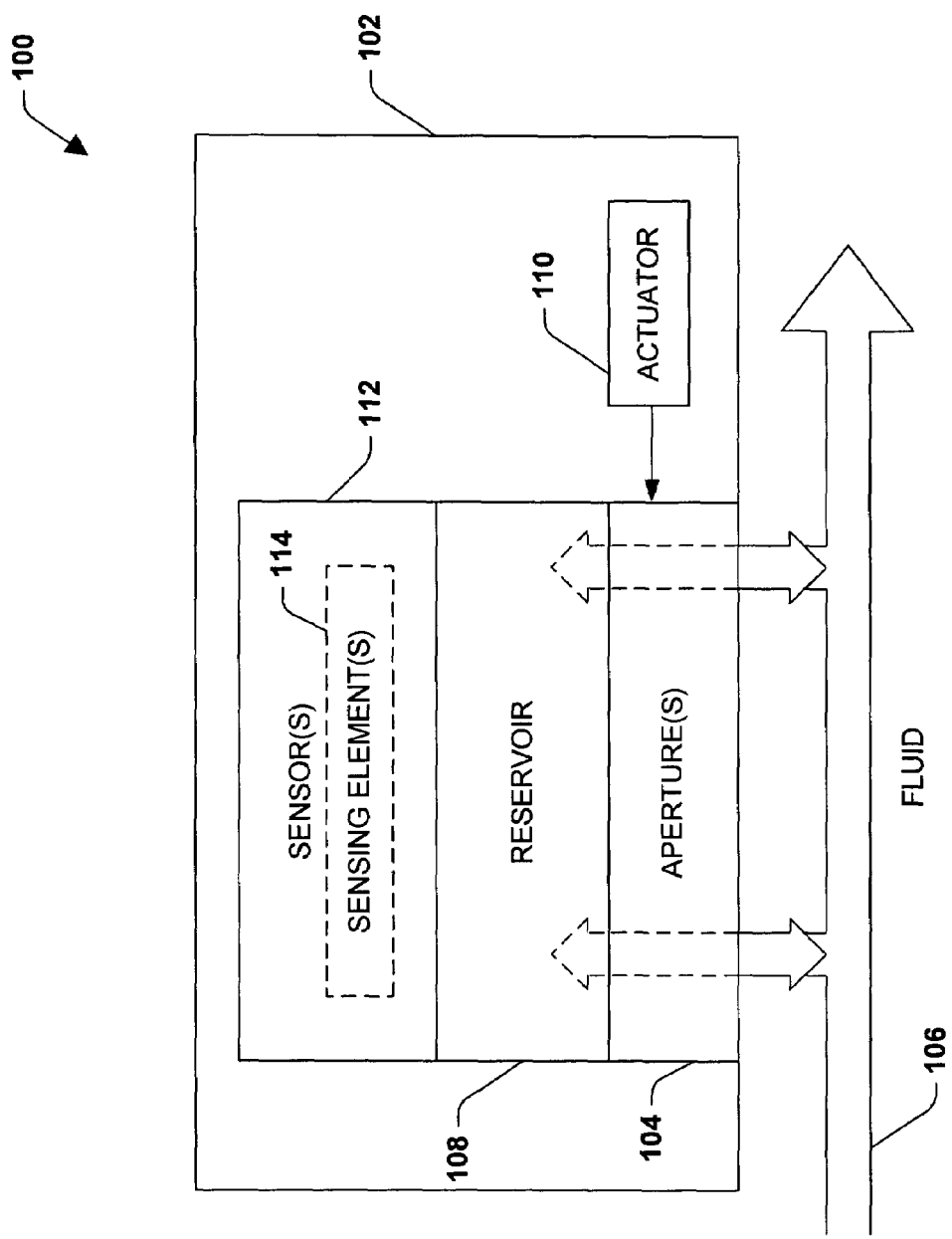
FIG. 1 is a block diagram of a system that facilitates measurement, analysis, and automatic maintenance of a fluid in machinery in accordance with an aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the term "computer component" is intended to refer to a computer-related entity, either hardware, a combination of hardware and software, software, or software in execution. For example, a computer component may be, but is not limited to being, a process running on a processor, a processor, an object, an executable, a thread of execution, a program, and/or a computer. By way of illustration, both an application running on a server and the server can be a computer component. One or more computer components may reside within a process and/or thread of execution and a component may be localized on one computer and/or distributed between two or more computers.

Referring now to the drawings, FIG. 1 illustrates a high-level system overview in connection with one particular aspect of the subject invention. The present invention relates to a novel system 100 for obtaining measurements of various parameters of fluid in machinery (e.g., oxidation level, TAN, temperature, viscosity, oxidation/reduction potential, . . . ), and thereafter employing such measurements in connection with automatically maintaining the fluid and/or adjusting current operation of the machinery. For example, oxidation level in a particular sample of fluid can be measured in real-time without requiring expensive and time-consuming laboratory testing. If an undesirably high level of oxidation is present, the present invention provides a system and/or methodology for chemically altering fluid chemistry, such as by injecting a determined amount of additive (e.g., antioxidant) and/or partially reversing such oxidation, thereby elongating useful life of the fluid. The system 100 can be utilized in rotating machinery, such as bearings, gearboxes, as well as other rotating and/or non-rotating machinery, including aircraft, land-based, space-based, and marine systems. While the present invention is hereafter described in connection with employment such invention in machinery, it is to be understood that the system and methodology described hereafter can be utilized in other contexts. For example, the present invention can be employed in connection with measuring parameters of biological fluids, drinking water, discharge water, cooking oils, process chemicals, etc.

The system 100 includes a casing 102 that can be mounted directly within a fluid flow line, pump, valve, filter, and/or reservoir of fluid. In accordance with one particular aspect of the present invention, the casing 102 can be a probe tip, which facilitates mounting the system 100 within intricate machinery. The casing 102 includes aperture(s) 104 that enables fluid 106 to enter a reservoir 108 within such casing 102. Alternatively, fluid can be directed to the reservoir 108 via small flow lines or other suitable device to the reservoir. Thereafter a pump mechanism can be employed to fill the reservoir 108 and/or purge the reservoir 108. The fluid 106 can be moving through a system (as illustrated in FIG. 1), or alternatively be located in a reservoir of fluid that is substantially larger than the reservoir 108. Once a significant sample of fluid 106 has entered the casing 102 via the aperture(s) 104, an actuator 110 is provided to facilitate closing the aperture(s) 104. One or more sensors (not shown) can be provided to determine a time when the actuator 110 should close the aperture(s) and to confirm that confined fluid 106 is not leaking from the reservoir 108. Furthermore, the one or more sensors can be utilized to determine that unaltered fluid 106 has been confined to the reservoir 108. Thus a particular unaltered sample of fluid 106 will be confined within the reservoir 108. In accordance with one aspect of the present invention, the casing 102 can be a cylindrical probe tip that comprises an outer cylinder, wherein a slight rotation of the outer cylinder causes the aperture(s) 104 to open and/or close (thus allowing fluid 106 to enter the reservoir 108 or confining fluid 106 within the reservoir 108). The actuator 110 can be employed to provide energy to rotate the probe tip, and the amount of energy required to rotate such tip can be utilized to determine one or more parameters of the fluid 106, such as sheer viscosity. In accordance with one aspect of the present invention, the actuator 110 can be a piezo-actuator, electromagnetic actuator, or other similar device motion structures.

Fluid 106 within the reservoir 108 will contact a sensor 112 that comprises one or more sensing elements 114. The sensing elements 114 can measure a plurality of parameters relating to the fluid 106, including but not limited to temperature, pH, TAN, SAN, oxidation/reduction potential, $H_2O$, oxidation levels, conductivity, ferrous contamination, additive state, chemical contaminants, etc. Confinement of a particular sample of fluid 106 provides for several substantial improvements over conventional in situ fluid sensing devices in that sensitive sensing elements 114 are protected from a moving fluid flowing over such sensing elements 114. In particular, the fluid 106 can contain various caustic elements and abrasive contaminants, such as flowing wear metal debris, that can damage the sensing elements 114 upon the fluid 106 flowing over such elements 114. Moreover, several parameters (including oxidation levels of fluid 106) require the fluid 106 to be unchanging near the sensor elements 114. For example, oxidation levels of fluid 106 can be determined via providing a plurality of electrodes as sensing elements 114 on the sensor 112. More particularly, a voltage source (not shown) can be provided to generate cyclically ramped voltages on a working electrode and a reference electrode (which surround a counter electrode) to induce a current in the counter electrode. The induced current varies depending upon the electro-chemical process occurring near the surface of the working electrode. Such voltages and currents can be employed to determine a present oxidation level in the fluid 106. Similarly, determining acidity of the fluid 106 (e.g., pH or TAN) requires fluid 106 proximate to the sensor elements 114 to remain unaltered for a period of time. Completion of the electrochemical process, however, can require a substantial amount of time. The system 100 enables effective measurement of oxidation levels, TAN, and other fluid parameters that require a significant time frame for satisfactory measurement.

In accordance with one aspect of the present invention, the system 100 can effectuate automatic maintenance of the fluid 106, thus extending useful life of the fluid. Such automatic maintenance lessens probability of human error in maintenance of the fluid 106 and reduces cost of replacing fluid with remaining useful life. For instance, parameters sensed by the sensing elements 114 can be relayed to a computing component (not shown) to effectuate analysis of the parameters and display of relevant information relating to the fluid (e.g., predictive remaining useful life of the fluid, oxidation levels of the fluid, acidity of the fluid, proposed maintenance measures, . . . ) to a maintenance engineer. The measured parameters can also be utilized in connection with automatically providing addition of fluid and/or fluid additives into a particular machine to reduce possibility of human error and extend the useful life of the fluid 106.

Furthermore, the system 100 can facilitate reduction of oxidation levels of the fluid 106 contained in the reservoir 108. Oxidation is an extremely prevalent parameter when referring to usefulness of a fluid as a lubricant. As oxidation levels of a fluid rise, usefulness of the fluid as a lubricant decline. The sensing elements 114 can be associated with three electrodes—a counter electrode that is surrounded by a working electrode and a reference electrode. As described infra, oxidation levels can be measured via providing a cyclical voltage to the working electrode and the reference electrode (e.g., −5 volts to 5 volts). An oxidation phase occurs due to a loss of electrons as voltages are applied, and a reduction phase occurs due to a gain of electrons. By applying a greater voltage for a greater amount of time during the reduction phase as compared to the oxidation phase, the oxidation present in the fluid 106 will be reduced. A more detailed example relating to reduction of oxidation in connection with the system 100 is provided supra. Upon obtaining satisfactory measurements of parameters relating to fluid 106 within the reservoir 108, the actuator 110 can effectuate opening of the aperture(s) 104 to release fluid 106 in the reservoir 108. For instance, a flushing mechanism can be provided to facilitate removal of the fluid 106 from the reservoir 108 through the aperture(s) 104. Thereafter another sample of fluid 106 can enter the casing 102 via the aperture(s), and parameters relating to the sample can be measured and/or analyzed.

The flushing mechanism can be comprises of any suitable established micro-fluidic devices such as miniature or micro-electric micro-pumps. The flushing mechanism can be an electrostatic and/or an electromagnetic piston diaphragm that forces that forces tested fluid out of the reservoir 108 and forces a new sample of fluid 106 into the reservoir 108. A dual or single element heater/cooler-temperature sensor can be provided to confirm replacement of tested fluid with untested fluid in the reservoir 108. Prior to purging and refilling the reservoir 108, the confined fluid 106 can be heated/cooled to a particular temperature (or the confined fluid 106 can be continuously heated/cooled). Monitoring temperature of the fluid within the reservoir 108 prior to utilizing the actuator 110 to close the aperture(s) 104 can facilitate confirmation that previously confined fluid 106 has been replaced by a new fluid sample.

Figure 2:
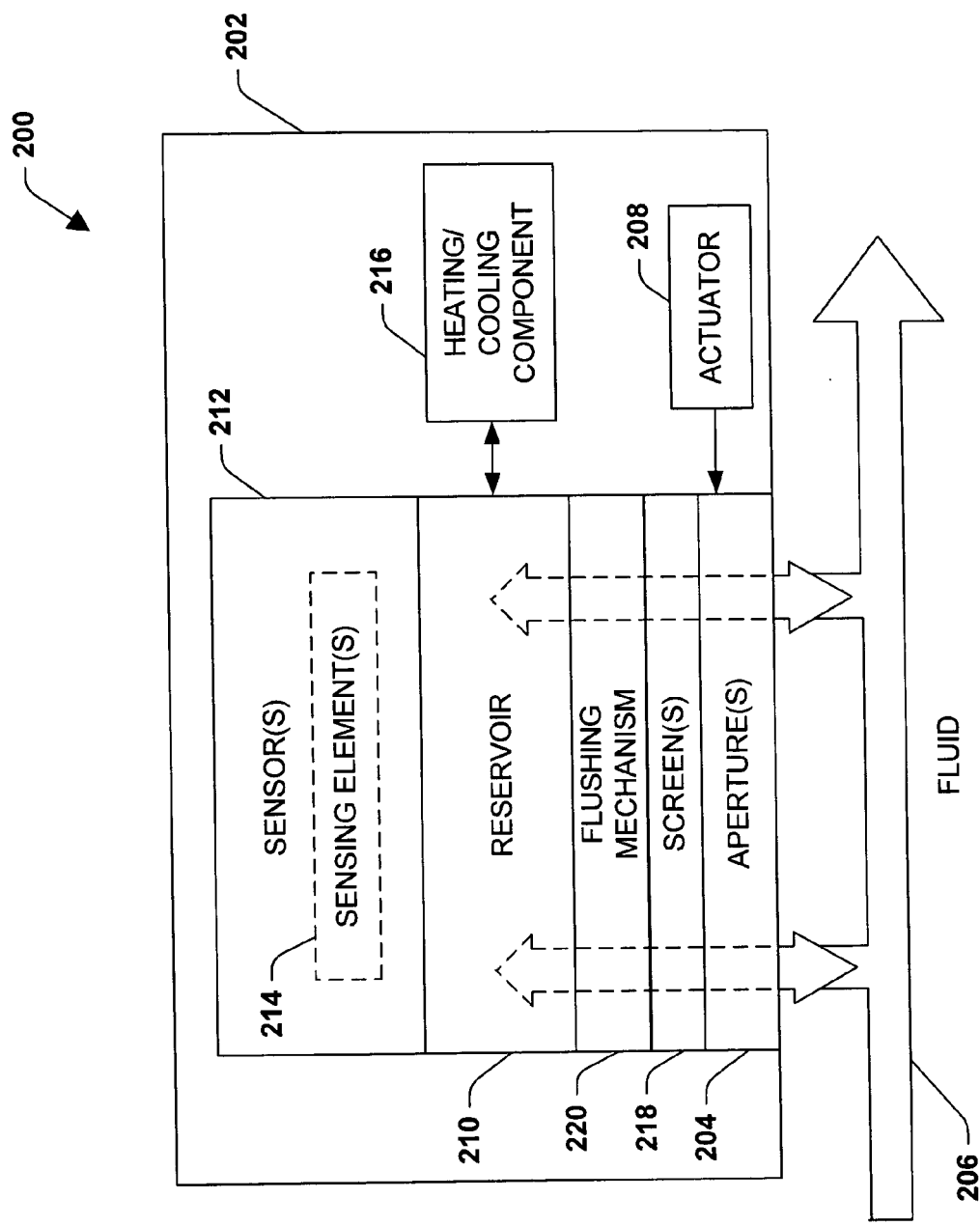
FIG. 2 is a block diagram of a system that facilitates measurement, analysis, and automatic maintenance of a fluid in machinery in accordance with an aspect of the present invention.

Referring now to FIG. 2, a system 200 that facilitates measurement, analysis, and automatic maintenance of fluid is illustrated. The system 200 includes a casing 202 that has aperture(s) 204, which enables a sample of a fluid 206 to enter the casing 202. An actuator 208 can be provided to open and close the aperture(s), which enables or prohibits fluid 206 from entering and leaving the casing 202. Upon passing through the open aperture(s) 204, the fluid 206 enters a reservoir 210 within the casing 202. The fluid 206 can flow through the aperture(s) 204 and into the reservoir 210 until the reservoir 210 is substantially filled, wherein the fluid 206 will be in contact with one or more sensor(s) 212. The aperture(s) 204 can then be closed, thereby confining a particular sample of the fluid 206 in the reservoir 210. The sensor(s) 212 includes one or more sensing elements 214, which facilitate measurement, analysis, and/or maintenance of the fluid 206. For example, the sensing elements 214 can include a three electrode electro-chemical sensor system (not shown) which measures oxidation levels in the fluid 206, and if necessary reduces oxidation levels in the fluid 206. Moreover, various other parameters of the fluid 206 can be measured via the sensing elements 214, such as temperature, acidity, conductivity, chemical contamination, ferrous contamination, additive depletion, etc. Such parameters can then be utilized in both preventative and predictive maintenance contexts. For instance, an alert can be relayed to a maintenance engineer if measured parameters reach predefined thresholds to facilitate preventative maintenance. Alternatively, measured parameters can be analyzed to predict a time in the future that maintenance will be required. Such information can be employed in connection with decision support functions such as production scheduling, automatic control adjustments, and mission planning.

A heating/cooling component 216 can be provided to modify temperature of the fluid 206 within the reservoir 210. Such temperature change can be utilized to test the sensor(s) 212 and the sensor element(s) 214, as well as to predict effects on the fluid 206 if an alteration in operation of the system occurs. For instance, an operator can desire to increase a rate of operation in system utilizing the fluid 206, thereby increasing temperature of the fluid 206. Testing the fluid 206 at particular temperatures can enhance accuracy of sensed parameters and can further improve analysis capabilities. Prior to effectuating such an enhanced rate of operation, the heating/cooling component 216 can heat a sample of the fluid 206 that is confined within the reservoir 210 and review parameters of the fluid 206 that are altered by the change in temperature. In conventional fluid measurement and analysis systems, in situ altering of temperature of a fluid was unavailable as fluids in a majority of systems are typically located in large reservoirs or do not remain static for a sufficient period of time to effectuate a desirable alteration in temperature. Heating and cooling of large reservoirs of fluid is ineffective, as a substantial amount of energy is necessary to alter temperature of a large reservoir of fluid, and such a large amount of energy can be damaging to a system (e.g., a significant amount of heat is required to raise a temperature of a large reservoir, which can damage heat-sensitive materials in a system), damaging to a process, and/or damaging to the fluid 206.

Screens 218 can also be provided to capture contaminants in the fluid 206 as it either enters and/or exits the casing 202 via the aperture(s) 204. For example, the fluid 206 may contain particles and/or contaminants that are harmful to the sensing elements 214, and the screens 218 can be placed in a manner to prevent such contaminants from entering the reservoir 210. Alternatively, as the fluid exists the reservoir 210 the screen(s) 218 can be employed to inhibit such contaminants from re-entering a fluid flow line or fluid reservoir (not shown), thus providing a maintenance mechanism for the fluid 206. Moreover, a flushing mechanism 220 can be provided to facilitate removal of fluid 206 from the reservoir 210 as well as to facilitate removal of contaminants from the screen(s) 218. For instance, the flushing mechanism 220 can be associated with a unit (not shown) for confining contaminants captured by the screen(s) 220. More particularly, the flushing mechanism 220 can utilize any suitable means for removing fluid 206 from the reservoir 210 and any contaminants from the screen(s) 218. Alternatively, natural forces (such as gravity, mechanism motion, or fluid flow in a system) can be utilized to remove fluid 206 from the reservoir 210, and the actuator 208 can be employed in connection with removing contaminants from the screen(s) 218. In accordance with one aspect of the present invention, the casing 202 can be a cylindrical probe tip, wherein the actuator 208 can rotate an outer cylinder to facilitate closing the aperture(s) 204. As the outer cylinder is rotated, a brush or other cleaning device can clean the screen(s) 218, and contaminants captured by the screen(s) 218 can be flushed back into the fluid 206 and/or removed from the fluid 206.

Figure 3:
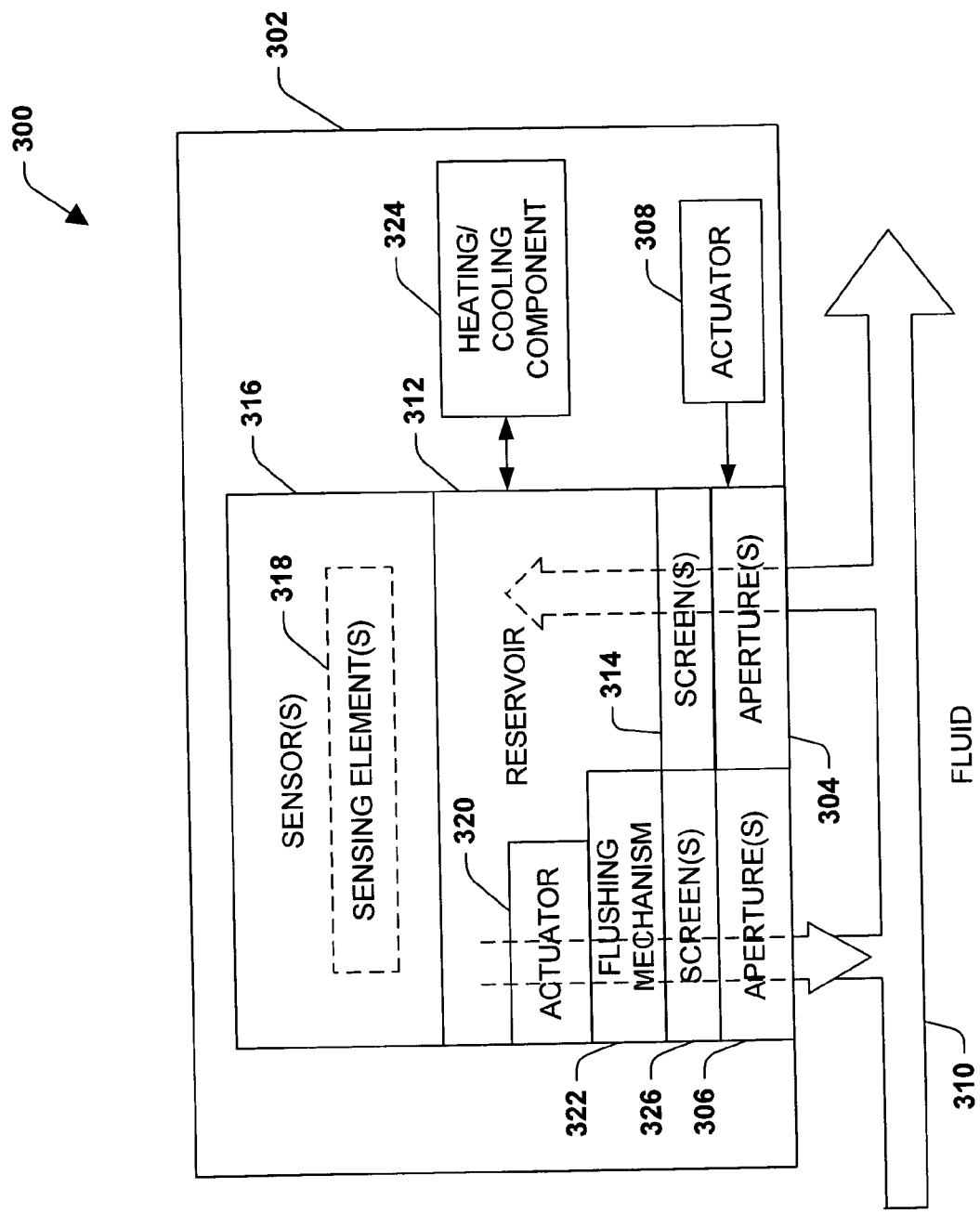
FIG. 3 is a block diagram of a system that facilitates measurement, analysis, and automatic maintenance of a fluid in machinery in accordance with an aspect of the present invention.

Now referring to FIG. 3, an exemplary system 300 that facilitates measurement, analysis, and automatic maintenance of fluids is illustrated. The system 300 includes a casing 302 that comprises aperture(s) 304 and 306. The aperture(s) 304 are opened by an actuator 308 to enable a fluid 310 to pass through the aperture(s) 304 and into a reservoir 312. Screen(s) 314 can optionally be provided to prevent contaminants and/or metal wear particles from entering the reservoir 312. The casing 302 further comprises one or more sensor(s) 316 that facilitate sensing and/or analysis of the fluid 310 within the reservoir 312. The sensor(s) 316 include sensing elements 318 that can sense a plurality of parameters of the fluid 310, such as temperature, pH, TAN, SAN, oxidation/reduction potential, $H_2O$, oxidation levels, conductivity, ferrous contamination, additive state, chemical contaminants, etc. Furthermore, a sensor (not shown) can be provided that is employed to determine when the reservoir 312 is sufficiently full of the fluid 310. Another actuator 320 is employed in connection with a flushing mechanism 322 to facilitate filling the reservoir 312 with a sample of the fluid 310. For instance, the flushing mechanism 322 can be a pump, compressed valve, or other similar device that can operate in connection with the actuator 322 to facilitate filling the reservoir 312 with the fluid 310.

Once the reservoir 312 is filled with the fluid 310, the actuator 308 can close the aperture(s) 304 to confine a sample of the fluid 310 within the reservoir 312. Various parameters of the confined sample of the fluid 310 can thereafter be sensed by the sensing elements 318. Moreover, a heating/cooling component 324 can be provided to heat and/or cool the sample of the fluid 310 within the reservoir 312. Confinement of the fluid allows the sensing elements 318 to measure parameters of a static, non-flowing fluid sample, which facilitates obtainment of accurate measurements. Moreover, as the confined sample of the fluid 310 will not be flowing across the sensing elements 318, sensing elements 318 will not be damaged by contaminants and/or metal wear particles in the fluid 310. Furthermore, altering temperature of the confined sample of the fluid 310 to particular temperatures and/or a series of particular temperatures facilitates obtaining more robust measurements via the sensing elements 318. In accordance with one aspect of the present invention, the sensing elements 318 can include a temperature sensor that can also act as the heating/cooling component 324.

Upon obtaining desired measurements, the actuator 308 can facilitate opening the aperture(s) 306 to enable the sample of the fluid 310 to exit the reservoir 312 and be placed into a main supply of the fluid 310. Utilizing two disparate aperture(s) or sets of aperture(s) for entrance of a sample of the fluid 310 into the reservoir 312 and exit of the sample of the fluid 310 from the reservoir facilitates timely and efficient exchange of fluid samples. For instance, natural forces such as gravity, rotation, etc. can exist that enable the fluid to easily enter the aperture(s) 304 while fluid exits the aperture(s) 306. The flushing mechanism 322 can be driven by the actuator 320 to effectuate efficient removal of the fluid 310 from the reservoir 312. Moreover, screen(s) 326 can be provided to capture contaminants in the fluid 310 to prevent such contaminants from re-entering a main fluid supply. It is to be noted that in the embedment illustrated in FIG. 3 that the actuator 308 facilitates opening and closing of the aperture(s) 304 and 306, while the actuator 320 is associated with the flushing mechanism 322 to assist in facilitating entrance of a sample of the fluid 310 into the reservoir 312 and exit of the sample of the fluid 310 from the reservoir 312. Thus the actuators 308 and 320 act independent of one another. Furthermore, screens 314 and 326 can be provided in connection with aperture(s) 304 and/or 306 (e.g., it is not required that screens be provided at fluid input and fluid output locations).

Figure 4:
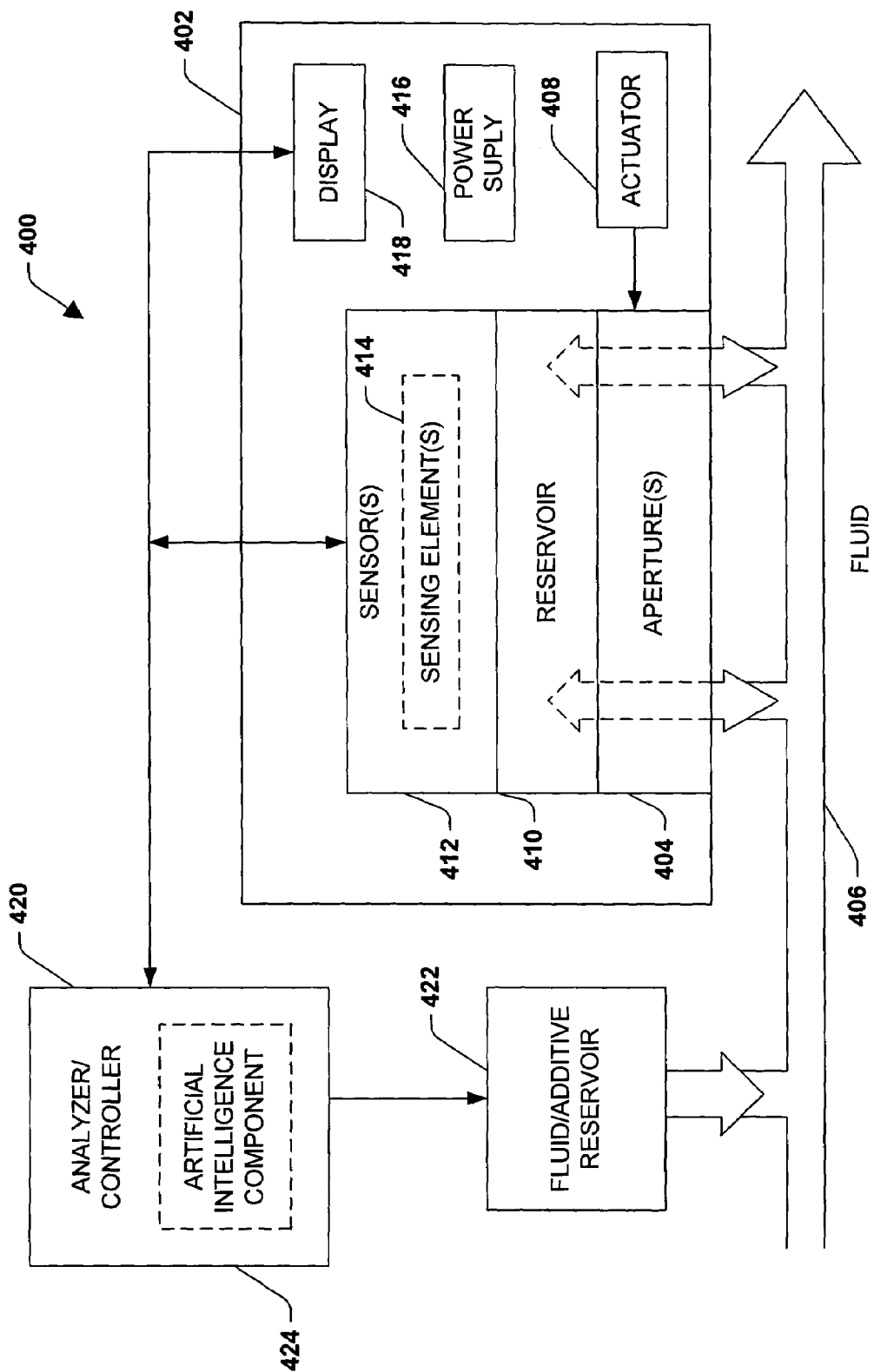
FIG. 4 is a block diagram of a system that facilitates measurement, analysis, and automatic maintenance of a fluid in machinery in accordance with an aspect of the present invention.

Turning now to FIG. 4, a system 400 that facilitates measurement, analysis, and automatic maintenance of fluids is illustrated. The system 400 includes a casing 402 that comprises one or more aperture(s) 404, wherein the aperture(s) enable fluid 406 that is utilized in a system to enter the casing 402. An actuator 408 is employed to open and close the aperture(s) 404 to allow fluid 406 to enter the casing 402, exit the casing 402, or confine the fluid 406 within the casing 402. Upon passing through the aperture(s) 404, the fluid 406 enters a reservoir 410 within the casing 402. The fluid 406 will contact one or more sensor(s) 412 that comprise at least one sensing element 414 upon substantially filling the reservoir 408. The sensing element(s) 414 can be employed to measure a plurality of parameters of the fluid 406, such as temperature, TAN, SAN, oxidation/reduction potential, $H_2O$, oxidation levels, conductivity, ferrous contamination, additive state, chemical contaminants, viscosity, etc. Furthermore, the sensing element(s) 414 can be employed to reduce oxidation levels within the fluid 406.

In accordance with one aspect of the present invention, the casing 402 can include a power supply 416 to provide power to the sensor(s) 414, a processor (not shown) a display unit 418, and the actuator 408, thus alleviating a need for an external power supply. The processor can be embedded in the casing 402 and act as an interface from measurements obtained by the sensing elements 414 and the display unit 418. The display unit 418 can receive measurements from the sensor(s) 414 and display such measurements to a maintenance engineer. For instance, the display unit 418 can indicate when fluid replacement is required, when a filter should be replaced, general health of fluid, etc. Thus a maintenance engineer can quickly view the display 418 and determine necessary maintenance steps. The display 418 can be mounted on the casing 402, or alternatively can be placed via a network to a location typical to the maintenance engineer.

In accordance with one aspect of the present invention, the power supply 416 can be integrated within the casing 402 and can consist of individual or a combination of storage batteries, storage capacitors, super capacitors, power scavenging devices, fuel cells, micro fuel cells, or inductively generated power from a changing magnetic field. Power scavenging techniques integrated within the casing 402 can include single or multiple power scavenging modalities including adaptive power scavenging. Power can be generated utilizing piezoelectric vibration, inductive, electro-thermal, photo voltage, fluid-based micro-turbine, piezoelectric pressure deviation, and/or electrochemical techniques. Stored electrical energy can include storage batteries such as corn cells or battery stacks, fuel cells and micro fuel cells such as nickel-hydride cells, or "printed" batteries such as can be printed on filter paper. The filter paper with printed batteries can be of a self-contained filter system including additional elements such as a power supply, sensor element, processor, memory display, communication(s), and actuator(s).

Measurements obtained from the sensor(s) 412 can also be received by an analyzer/controller 420 that utilizes the measurements to analyze and automatically maintain the fluid 406. The analyzer/controller 420 can employ any suitable control logic to implement automatic maintenance of the fluid 406, including data fusion techniques, data trending techniques, and system modeling and control methods. For example, the analyzer/controller 420 can utilize the measurements obtained by the sensor(s) 412 to replenish the fluid 406, thereby automatically maintaining a desirable fluid amount. The analyzer/controller 420 can relay control commands to a fluid/additive reservoir 422 to add a desirable amount of fluid/additive to fluid 406 presently within a machine. Moreover, the analyzer/controller 420 can analyze sensor measurements to determine that a particular parameter of fluid 406 requires modification for optimal operation of a machine. The analyzer/controller 420 can thereafter relay control commands to the fluid/additive reservoir 422 to add a desirable additive to the fluid 406. Such automatic maintenance of the fluid 406 lessens a probability of human error in maintaining fluid in a system. It is to be understood that the analyzer/controller 420 can utilize a model-based approach to analyzing and altering fluid chemistry. For instance, the analyzer/controller can employ a chemical model, an electrochemical model, a prognostics model, and various other suitable models to facilitate analysis and automatic maintenance of fluids. One particular data fusion technique that can be employed in connection with the present invention is described in U.S. Pat. No. 6,286,363, entitled INTEGRATED MULTI-ELEMENT LUBRICATION SENSOR AND HEALTH LUBRICANT ASSESSMENT SYSTEM, which as mentioned above is hereby incorporated by reference in its entirety.

In accordance with another aspect of the present invention, the analyzer/controller 420 and the fluid/additive reservoir 422 can be employed to alter chemical composition of a sample of the fluid 406 confined within the reservoir 410. For instance, the analyzer/controller can determine an amount of additive (e.g., antioxidant) if any to inject into the sample of fluid within the reservoir 410. Thereafter voltammetric techniques can be employed to oxidize the confined sample and thereafter reduce the confined sample utilizing a three-electrode electrochemical sensor. A degree of oxidation present in the confined sample can thereafter be analyzed together with an amount of additive injected into the sample. Such a method facilitates verification of TAN, TISN, sensor performance, performance of device utilized to inject additives, self calibration, etc. Furthermore, a miniature titration process can be performed on the confined sample of fluid, which duplicates precision of ASTM tests for TAN, TBB, SAN. Moreover, alteration of the confined fluid can be a miniature reclamation process that confirms that fluid reclamation is possible. Such alteration of a confined sample can also be a basis of continuous, dynamic reclamation as required and/or sensed.

In accordance with one aspect of the present invention, the fluid/additive reservoir 422 can be associated with MEMs valves or small electrical actuators that are responsive to the analyzer/controller 420 to facilitate introduction of additional fluid to remedy a low-fluid condition and/or replenish a chemically depleted fluid with fluid additives. Alternatively, the fluid/additive reservoir can be a pressurized vessel that momentarily opens an electric valve that will permit metering of a prescribed amount of fluid. Furthermore, upon sensing a change in operating procedure or environment, the analyzer/controller 420 can relay commands to the fluid/additive reservoir 422 to alter a chemical composition of the fluid 406 (e.g., increase or decrease in temperature, particular contaminant in the fluid 406, ... ). As a plurality of sensing element(s) 414 can be employed in connection with the system 400, quality and accuracy of sensor data, analysis and results derived from the sensor data, and fluid adjustment can be efficiently determined. For instance, data quality metrics can be incorporated into the sensor(s) 412 logic. Moreover, as quality of fluid analysis can change over time based upon time between calibrations, degradation of the sensing element(s) 414, failure of a sensing element 414, etc., the system 400 can output an obtained measurement from the sensing element(s) 414 as well as an estimate of the quality of the measurement (e.g., degree of certainty or plus or minus 5%). The analyzer/controller 420 can also be employed to control operation of machinery utilizing the system 400. For example, if bearing lubrication is depleted and temperature is above a desirable level, the analyzer/controller 420 can limit rotational speed of the bearing, which will extend useful life of the fluid as well as avoid mechanically damaging the bearing. In another example, a maximum compressor speed and/or compressor pressure within an air condition system can be limited, thereby reducing rate of Freon degradation or Freon leakage.

The analyzer/controller 420 can be associated with an artificial intelligence component 424 to effectuate robust automatic predictive maintenance of the fluid 406. The artificial intelligent component 424 can infer actions desirably taken in connection with maintaining the fluid 406. 4444As used herein, the term "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification schemes and/or systems (e.g., support vector machines, artificial neural networks, expert systems, Bayesian belief networks, fuzzy logic, data fusion engines . . . ) can be employed in connection with performing automatic and/or inferred action in connection with the subject invention.

For example, the artificial intelligence component 424 can "learn" that during particular time frames of particular days a rotating machine utilizing the fluid 406 is operated at a substantially greater rotation rate. Thus, via utilizing the artificial intelligence component 424 the analyzer/controller 420 can maintain the fluid 406 in a predictive manner to enable optimal operation of a machine and extend useful life of the fluid 406 without requiring machine shut down. The artificial intelligence component 424 can also effectuate display of predictive and/or preventative maintenance via the display 418. For instance, the artificial intelligence component 424 can display various parameters in a particular manner given a user state and context (e.g., a first maintenance engineer may desire to view parameters differing from those desirably viewed by a second maintenance engineer or an operations supervisor or production planner). Moreover, the artificial intelligence component 424 can infer a quality estimate of measured parameters based on historical data, user state and context, sensor and fluid physics, sensor fusion, and various other parameters relating to measurement of fluid. It is to be further noted that the analyzer/controller 420 and/or the artificial intelligence component 424 and/or the fluid/additive reservoir 422 can be integrated within the casing 402.

Figure 5:
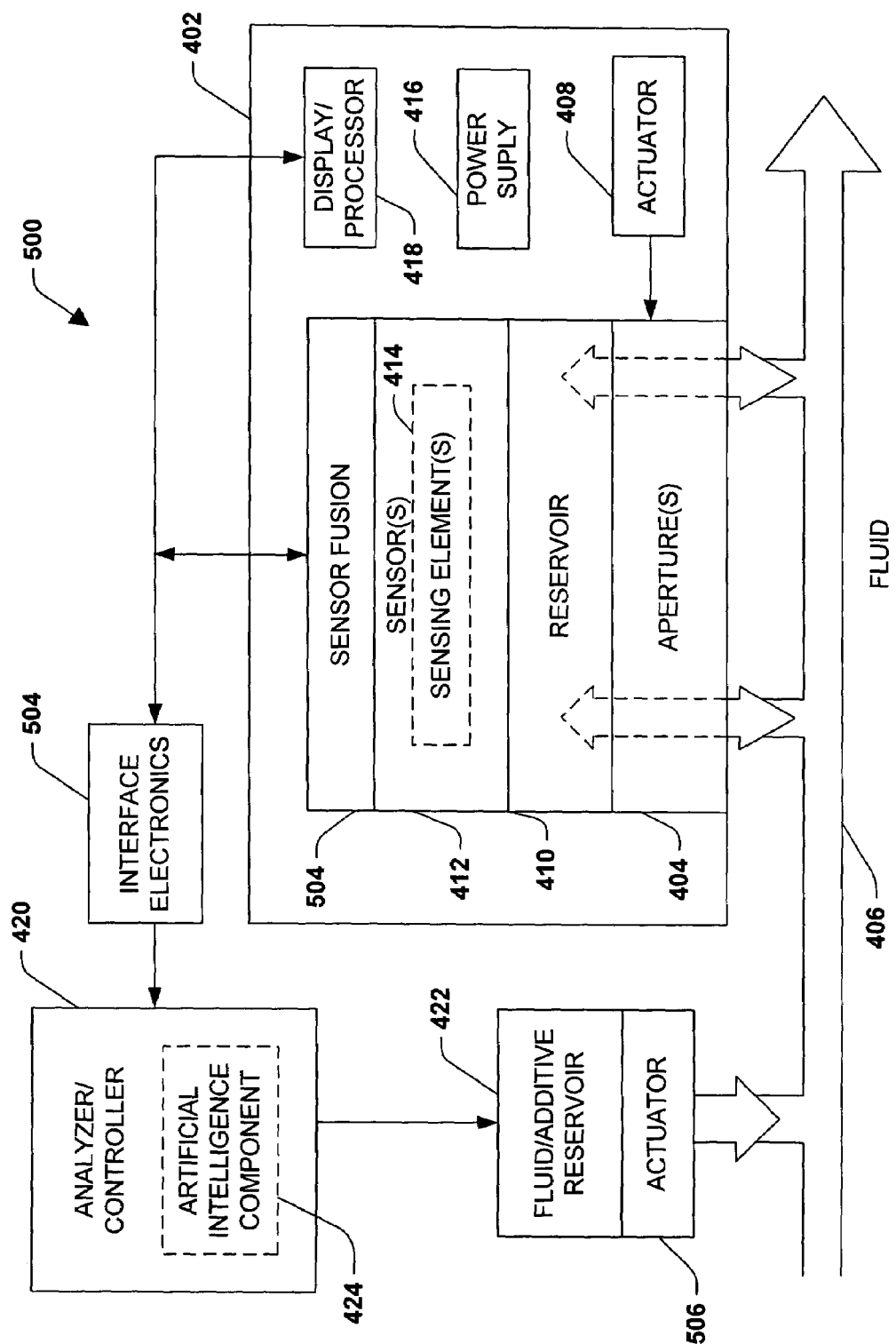
FIG. 5 is a block diagram of a system that facilitates measurement, analysis, and automatic maintenance of a fluid in machinery in accordance with an aspect of the present invention.

Now turning to FIG. 5, a system 500 is illustrated that facilitates measurement, analysis, and automatic maintenance of a fluid is illustrated. The system 500 includes various components present in the system 400 illustrated in FIG. 4, and for sake of brevity discussion of such components is omitted. Like numerals refer to like components as discussed with respect to FIG. 4. The system 500 further comprises a sensor fusion component 502 that facilitates fusion of data obtained by the sensing elements 414, to thereby obtain a robust analysis of the fluid 406. For example, the sensor fusion component 502 enables determination of parameters not directly measured by the sensing elements 414, such as lubricity, as well as provides for more accurate measurements. Data fused by the sensor fusion component 502 can then be relayed to the analyzer/controller 420 via interface electronics 504. The interface electronics 504 can comprise a processor, analogue circuitry, and any other suitable circuitry for interfacing fused data to the analyzer/controller 420. Moreover, it is to be understood that the interface electronics 504 can be integrated within the casing 402 to enable substantially autonomous measurement, analysis, and/or automatic maintenance of the fluid 406.

The analyzer/controller 420 can then effectuate altering chemical composition of the fluid 406 in a main supply of fluid via relaying control commands to the fluid/additive reservoir 422. The fluid/additive reservoir includes an actuator 506 that is responsive to control commands relayed from the analyzer/controller 420. For example, the analyzer/controller 420 can employ data obtained by the sensing elements 414 to output commands relating to alteration of volume and/or chemical composition of a main supply of the fluid 406. The actuator 506 can be responsive to the control commands and facilitate addition of fluids and/or additives from the fluid/additive reservoir 422. For instance, the actuator 506 can be a valve that enables particular amounts of fluid and/or additives to exit the fluid/additive reservoir 422 and enter a main supply of the fluid 406. Furthermore, it is to be understood that the analyzer/controller 420 can be integrated into the casing 402 and further integrated with the sensors 412 and the interface electronics 504.

Figure 6:
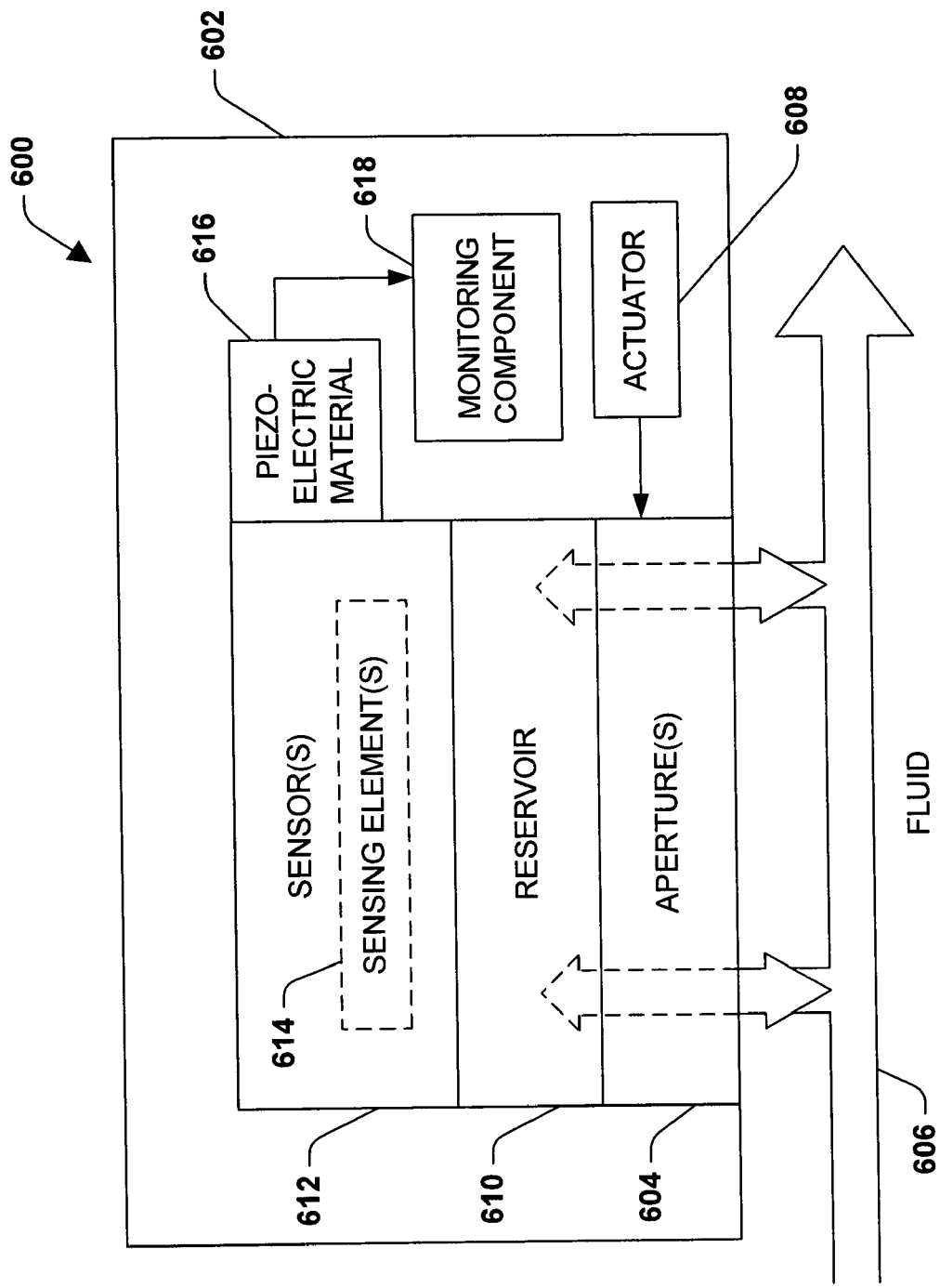
FIG. 6 is a block diagram of a system that facilitates measurement, analysis, and automatic maintenance of a fluid in machinery in accordance with an aspect of the present invention.

Referring now to FIG. 6, a system 600 that facilitates measurement, analysis, and automatic maintenance of a fluid is illustrated. The system 600 comprises a casing 602 containing one or more aperture(s) 604. The aperture(s) 604 enable a fluid 606 to enter the casing 602 during instances that the aperture(s) 604 are open. An actuator 608 is employed to both open and close the aperture(s), thus enabling entrance of the fluid 606 into the casing 602 and confinement of a sample of the fluid 606 (e.g., the aperture(s) 604 remain open until a desired sample of the fluid 606 enters the casing, and thereafter the actuator 608 is utilized to close the aperture(s) 604 to confine the sample of the fluid 606 within the casing 602). When the aperture(s) 604 are open, a sample of the fluid 606 can enter the casing 602 into a reservoir 610. The sample of the fluid 606 will substantially fill the reservoir 610, causing the fluid 606 to become proximate to one or more sensor(s) 612 that includes one or more sensing element(s) 614. The sensing element(s) 614 can be employed to measure various parameters of the sample of the fluid 606, such as temperature, oxidation level, pH, TAN, SAN, oxidation/reduction potential, $H_2O$, oxidation levels, conductivity, ferrous contamination, additive state, chemical contaminants, conductivity, and various other parameters relating to the fluid 606. Confinement of a sample of the fluid 606 enables reliable real-time in situ measurement of fluid parameters.

The system 600 can further comprise piezoelectric material 616 that can be employed to measure an amount of vibration of the system 600, as well as provide a source of power to the sensor(s) 612 and the sensor element(s) 614. Piezoelectricity refers to an ability of particular materials to produce a voltage when subjected to mechanical stress and/or strain. Within the piezoelectric material 616, positive and negative electrical charges are separated, but symmetrically distributed, thereby rendering the piezoelectric material 616 neutral. Upon applying a stress and/or strain, the symmetry is destroyed and the charge asymmetry generates a voltage. As the piezoelectric material 616 generates a voltage when distorted via application of stress and/or strain, the piezoelectric material can be utilized in connection with measuring vibration causing the stress and/or strain. For example, distortions can occur in the piezoelectric material 616 upon being subject to vibration, thereby resulting in generation of voltages from the piezoelectric material 616. Such voltages can be monitored by a monitoring component 618 and utilized in connection with determining vibration and/or providing power to the sensor(s) 612 and sensing element(s) 614. Moreover, a control component (not shown) can utilize vibration measurements to control operation of a machine comprising the system 600. Such a control component can thus hold vibration within acceptable threshold values. Furthermore, the piezoelectric material 616 can be employed to measure viscosity and/or density of a fluid via immersing the piezoelectric material in the fluid 606. The aforementioned properties of the piezoelectric material 616 (e.g., distortion upon an application of voltage, generating voltage upon distortion, . . . ) can effectuate dynamic monitoring of vibration as well as feedback control to control vibration. Vibration of a monitored structure can be accomplished for a motor-driven system via altering rotational speed of a motor. Avoiding operation at a critical speed or quickly passing through a critical speed will limit machinery vibration. The critical speed of a system is a speed that excites or resonates at the natural frequency of the system. Alternatively, vibration can be minimized via active control methods such as active vibration cancellation. Data from the sensing elements 614 can be combined using sensor fusion. Vibration information from the piezoelectric material can also be combined with readings from the sensor elements 614. Sensor fusion methods such as explicit fluid spectrums, artificial neural networks, and/or empirically derived models can be employed in connection with the present invention. Sensor fusion can be utilized to generate new, perhaps unmeasured quantities (e.g., lubricity), refine and/or improve obtained measurements (e.g., water content), determine existence of failed or failing sensor elements, and validate a believe in fluid failure states and/or lubricant conditions (e.g., wear metals present). The piezoelectric material 616 can be any suitable material that outputs sufficient voltage upon being distorted, such as crystals of tourmaline, quarts, topaz, cane sugar, Rochelle salt, quartz analogue crystals (e.g., $ALPO_4$, $GaPO_4$, . . . ), ceramics with perovskite or tungsten-bronze structures (e.g., $BaTiO_3$, $KNbO_3$, $LiNbO_3$, $LiTaO_3$, $BiFeO_3$, $Na_xWO_3$, $Ba_2NaNb_5O_{15}$, $Pb_2KNb_5O_{15}$, . . . ), polymer polyvinlidene fluoride ($—CH_2—CF_2—$)$_n$, etc.

In accordance with one aspect of the present invention, commercially available piezoelectric ceramics such as PZT, PLZT and PMN-PT can be utilized to effectively measure and/or control vibration of a machine, as well as provide power to the sensor(s) 612 and sensing element(s) 614. More specifically, a Nb-doped PLZT having a general formula $(Pb_{1-x}La_x)(Zr_yTi_{1-y})_{1-(x/4)}O_3$, wherein x approximately equals 0.07 and y approximately equals 0.60, can be utilized in connection with the present invention. The ceramic can be fabricated by a hot forging technique utilizing PbO, $TiO_2$, $ZrO_2$, and $La_2O_3$ powders as starting materials with $Nb_2O_5$ added to provide 0.5–1.5% $Nb^{5+}$ (mole % as dopant). Moreover, the ceramic can be fabricated via mixing appropriate weights of the aforementioned materials. For example, 163 units of PbO, 9 units of $La_2O_3$, 56 units of $ZrO_2$, 24 units of $TiO_2$, and 1 unit of $Nb_2O_5$ can be mixed to fabricate the aforementioned ceramic.

Such ceramic exhibits a strong dialectric-permittivity maximum at approximately 155°–160° C., above and below which the permittivity drops rapidly. The ceramic becomes a polar dialectric below about 112°–125° C., exhibiting a stable net spontaneous polarization, $P_r$, and a well-defined polarization hysteresis loop (P versus bipolar electric field). As compared with conventional piezoelectric ceramics, such an Nb-doped PLZT ceramic has reduced strain hysteresis with application of a unipolar electric field. In addition, breakdown strengths of these PLZT ceramics are greater than about 25 kV/cm (generally 25–30 kV/cm), well above typical operating electric field strengths that are normally used for piezoelectric actuation. Furthermore, a linear piezoelectric coefficient ($d_{33}$), the maximum strain (%), and fatigue life (cycles) of the Nb-doped PLZT ceramic materials are significant advances over other piezoelectric materials.

In accordance with another aspect of the present invention, a PLZT ceramic having a general formula $(Pb_{1-x}La_x)(Zr_yTi_{1-y})_{1-(X/4)-z}M^{a+}_{4z/a}O_3$ can be utilized within the system 600, wherein x approximately lies between 0.04 to 0.05, y approximately lies between 0.52 and 0.58, z approximately lies between 0.04 and 0.06, and M is a combination of Nb and Ta, $a^+$ being the valence of Nb and Ta respectively. Such a ceramic is fabricated via a hot forging technique utilizing PbO, $TiO_2$, $ZrO_2$, and $La_2O_3$ powders as starting materials. $NbO_2$ and $Ta_2O_5$ are added to provide 2.0–3.0% $Nb^{5+}$ (mole %) as dopants. The resulting materials have an average grain size of about 3 μm, a well defined polarization hysteresis loop, reduced strain hysteresis when a unipolar electric field is applied, a breakdown strength of greater than 26 kV/cm, a linear piezoelectric strain coefficient ($d_{33}$) greater than 700 pC/N, maximum strain greater than 0.15%, a coupling constant ($k_{33}$) of 0.81 and a fatigue life of at least $10^9$ cycles. Furthermore, performance of aforementioned PLZT ceramic surpasses that of other available commercial photoelectric materials.

A particular formula of one PLZT ceramic has lanthanum, zirconium, and tantalum in molar ratios of 4.5, 55, and 45 respectively (4.5/55/45) resulting in $(Pb_{0.955}La_{0.045})(Zr_{0.55}Ti_{0.45})_{0.93875}O_3$ with Nb and Ta dopants adding an additional 4 to 6 mole %, preferably 2.5 mole % of Nb and 2.5 mole % of Ta. Such a ceramic can be fabricated by mixing 99.069 units of PbO, 3.340 units of $La_2O_3$, 28.893 units of $ZrO_2$, 15.473 units of $TiO_2$, 1.211 units of $Nb_2O_3$, and 2.014 units of $Ta_2O_5$. The PLZT ceramic exhibits a strong dialectric-permitivity maximum at approximately 200–215° C. Nb/Ta doped PLZT becomes a polar dialectric below about 205–208° C., which is much higher than other piezoelectric materials fabricated in a substantially similar manner, while still exhibiting a stable net spontaneous polarization, $P_r$, and a well-defined, small polarization hysteresis loop (P versus bipolar electric field). Similar to other Nb-doped PLZT ceramics, Nb/Ta-doped ceramics of the present invention also have reduced strain hysteresis with application of a unipolar electric field. In addition, breakdown of these PLZT ceramic materials is greater than about 30 kV/cm (generally 28–32 kV/cm), comparable to typical operating electric field strengths that are normally exhibited by piezoelectric actuation of materials that can not operate at higher temperatures. Furthermore, Nb/Ta-doped PLZT ceramic materials do not show degradation in operating properties, including linear piezoelectric coefficient ($d_{33}$), maximum strain (%), and fatigue life (cycles) when operated at temperatures up to about 200° C.

Figure 7:
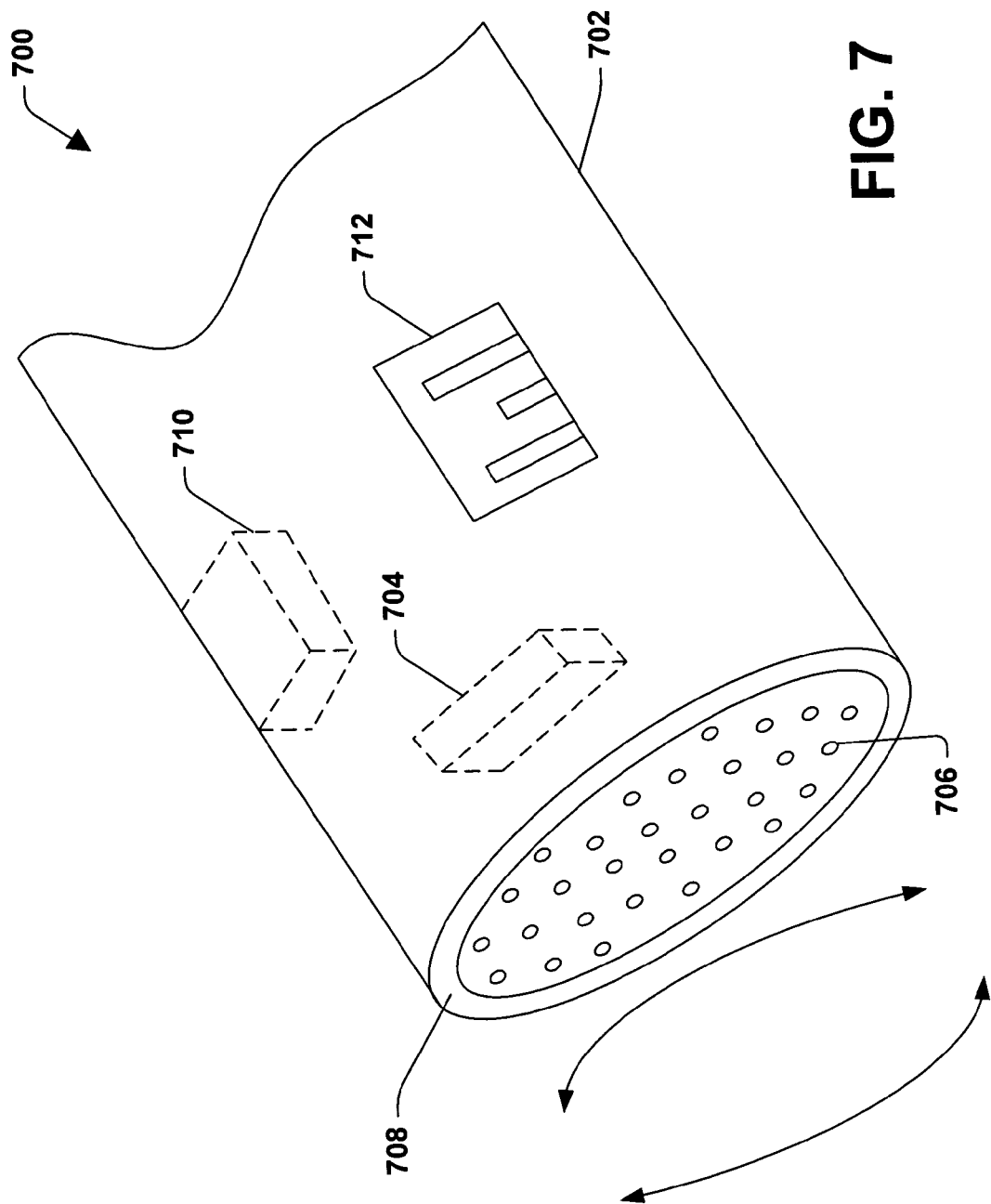
FIG. 7 is an exemplary environment in which the present invention can operate in accordance with an aspect of the present invention.
Figure 8:
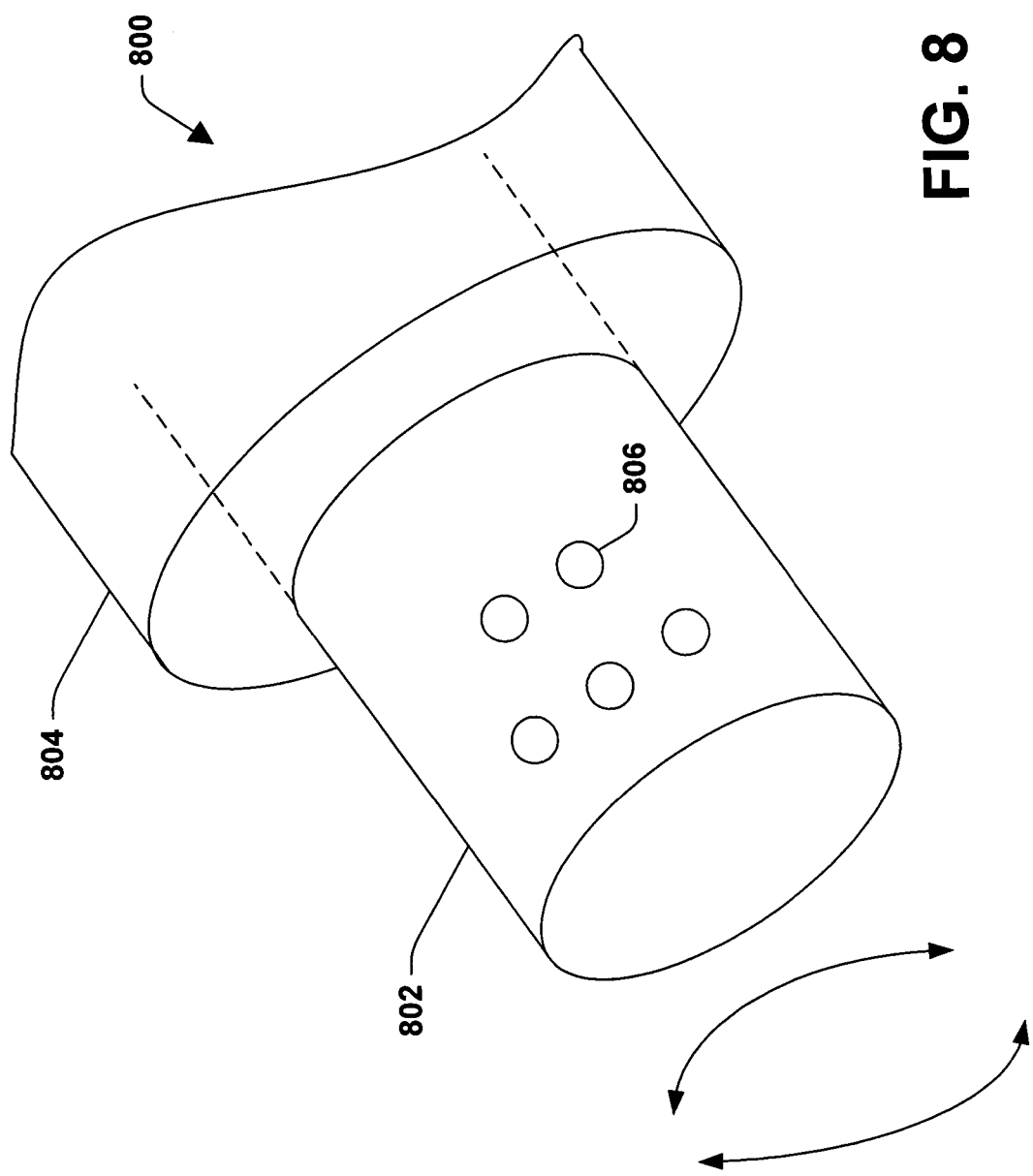
FIG. 8 is an exemplary environment in which the present invention can operate in accordance with an aspect of the present invention.

Now turning to FIG. 7, an exemplary system 700 that facilitates real-time in situ measurement and analysis of various parameters of a fluid, as well as automatic maintenance of the fluid, is illustrated. The system 700 comprise(s) a probe tip 702 that contains one or more multi-element fluid sensor(s) 704 which can obtain measurements of various parameters of fluid, including viscosity, acidity, and electrochemical analysis. The probe tip 702 can be mounted within machinery to facilitate integration of the sensor(s) 704 into a particular piece of machinery. The probe tip 702 can include apertures 706 that enable fluid to flow into the probe tip 702 and contact the sensor(s) 704. An actuator (not shown) can be utilized to open the aperture(s) 706, thereby allowing fluid to enter the probe tip 702. The probe tip 702 will fill with fluid until such fluid contacts the sensor(s) 704, wherein the actuator will close the aperture(s) 706 to confine a sample of the fluid within the probe tip 702. Once the fluid is confined, various testing can be performed on the non-flowing, static fluid sample. The aperture(s) 706 can thereafter be opened, and the fluid within the probe tip 702 can be flushed. A sequence of opening the aperture(s) 704, confining a sample of fluid, closing the aperture(s) 704, testing the fluid, and re-opening the aperture(s) to flush the fluid sample and obtain another fluid sample can be repeated regularly to continually test fluid in a reservoir or within a flowing pathway of fluid.

In accordance with one aspect of the present invention, the actuator opens the aperture(s) 706 via rotating an outer cylinder 708 of the probe tip. The amount of energy required to rotate the outer cylinder 708 can correlate to viscosity of fluid in which the probe tip 702 is immersed. Moreover, the probe tip 702 can contain a power source 710 to enable continuous sampling and testing of fluids such as lubricating fluid, hydraulic fluid, oil, grease, fuels, etc. A display 712 can be placed on the outside of the probe tip 702 to convey to a maintenance engineer information regarding remaining lifetime of a fluid before fluid replacement is required, lifetime of a filter, etc. Furthermore, it is to be understood that the system 700 can be employed in connection with automatically maintaining fluid, wherein a sample of the fluid is tested by the sensor(s) 704 within the probe tip. For instance, measurements obtained by the sensor(s) can be utilized to control operation of machinery, as well as automatically replenish fluid and alter chemical composition of fluid according to historical use and present operation. Moreover, the sensor(s) 704 can effectuate reversal of oxidation of fluid that is confined within the probe tip 702, as well as measure current oxidation levels of fluid.

Referring now to FIGS. 8–12, exemplary embodiments in which the present invention can be employed are illustrated. First turning to FIG. 8, a probe tip 800 that can be employed in connection with practicing the present invention is illustrated. The probe tip 800 comprises two cylinders 802 and 804, respectively, wherein the first cylinder 802 can be rotated with respect to the second cylinder 804. Upon rotating the first cylinder 802, a plurality of aperture(s) 806 are opened, thereby allowing fluid to flow into a reservoir (not shown) within the first cylinder 802. Rotating the first cylinder 802 with respect to the second cylinder 804 again (in the same direction as before or in an opposite direction) facilitates closing the apertures 806, thus confining a sample of fluid within the first cylinder 802. Sensing elements, fusion components, heating/cooling components, a controller/analyzer, and other components discussed previously can be embedded within the probe tip 800 to facilitate robust measurement, analysis, and/or automatic maintenance of fluid.

Figure 9:
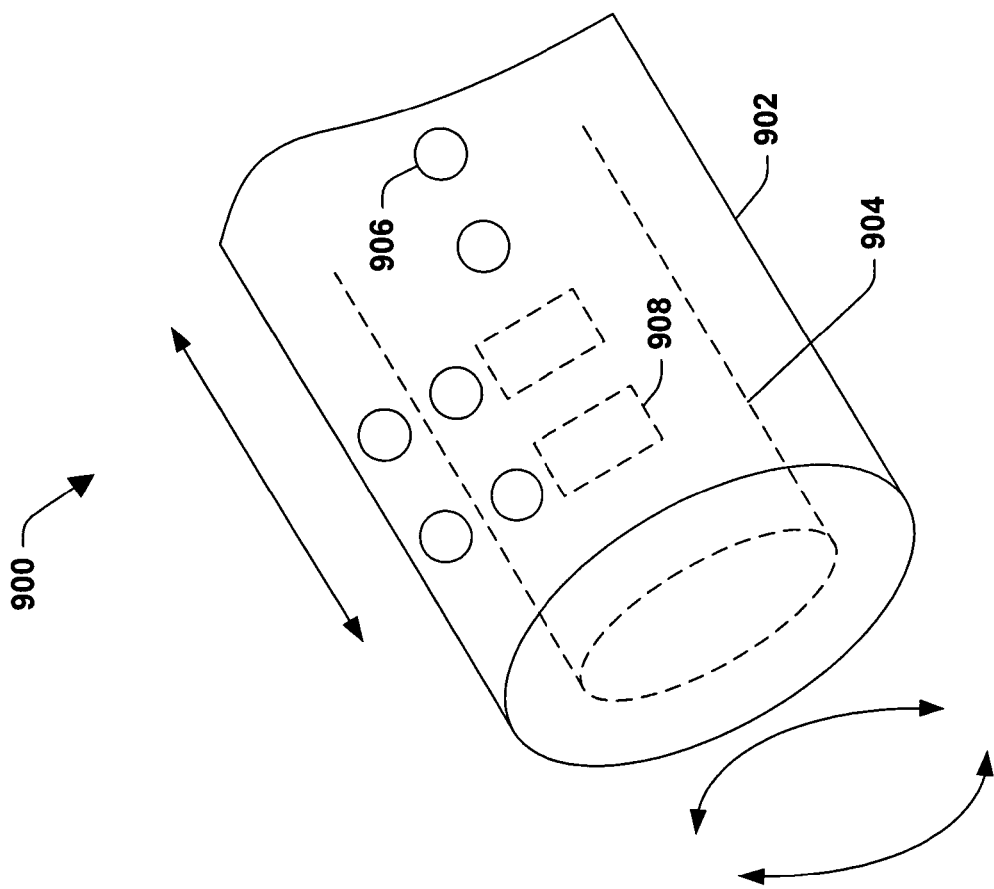
FIG. 9 is an exemplary environment in which the present invention can operate in accordance with an aspect of the present invention.

Now regarding FIG. 9, another exemplary probe tip 900 that can be employed in connection with practicing the present invention is illustrated. The probe tip 900 comprises an outer cylinder 902 and an inner cylinder 904, wherein the outer cylinder includes aperture(s) 906 and the inner cylinder includes slots 908. Upon rotating the outer cylinder 902 with respect to the inner cylinder 904, the apertures 906 can be aligned with the slots 908, thereby enabling a pathway for fluid to enter/exit the inner cylinder. Alternatively, the outer cylinder 902 can be moved axially with respect to the inner cylinder 904, thereby aligning the apertures 906 with the slots 908. Upon rotating the outer cylinder 902 with respect to the inner cylinder 904 in a substantially similar and/or opposite direction, the aperture(s) 906 and the slots 908 can be misaligned, thereby preventing an exit of fluid from the inner cylinder 904 and entrance of fluid into the inner cylinder 904. Alternatively, the outer cylinder 902 can be moved axially with respect to the inner cylinder 904 to facilitate misalignment of the apertures 906 and the slots 908. Such a mechanical orientation facilitates confining a sample of fluid within the inner cylinder 904, and the sample of fluid can thereafter be analyzed to facilitate automatic maintenance of a main supply of fluid.

Figure 10:
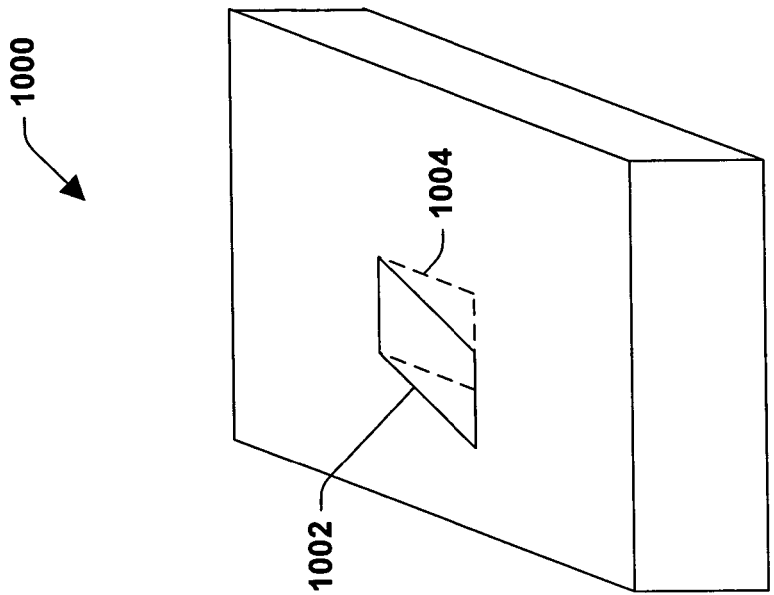
FIG. 10 is an exemplary environment in which the present invention can operate in accordance with an aspect of the present invention.

Turning now to FIG. 10, an exemplary device 1000 that can be employed in connection with confining a sample of fluid is illustrated. The device 1000 includes a flap 1002 that can be lifted to expose an aperture 1004, wherein fluid can flow through the aperture and into a reservoir (not shown) within the device 1000. An actuator (not shown) can be provided to facilitate opening the flap 1002 during instances that it is desirable for fluid to enter and/or exit the device 1000. The flap can thereafter be closed to prevent entrance and/or exiting of fluid into/from the device 1000. Thus, a sample of fluid can be confined within the device 1000, and robust measurement and/or analysis techniques as discussed herein can be performed on the confined fluid.

Figure 11:
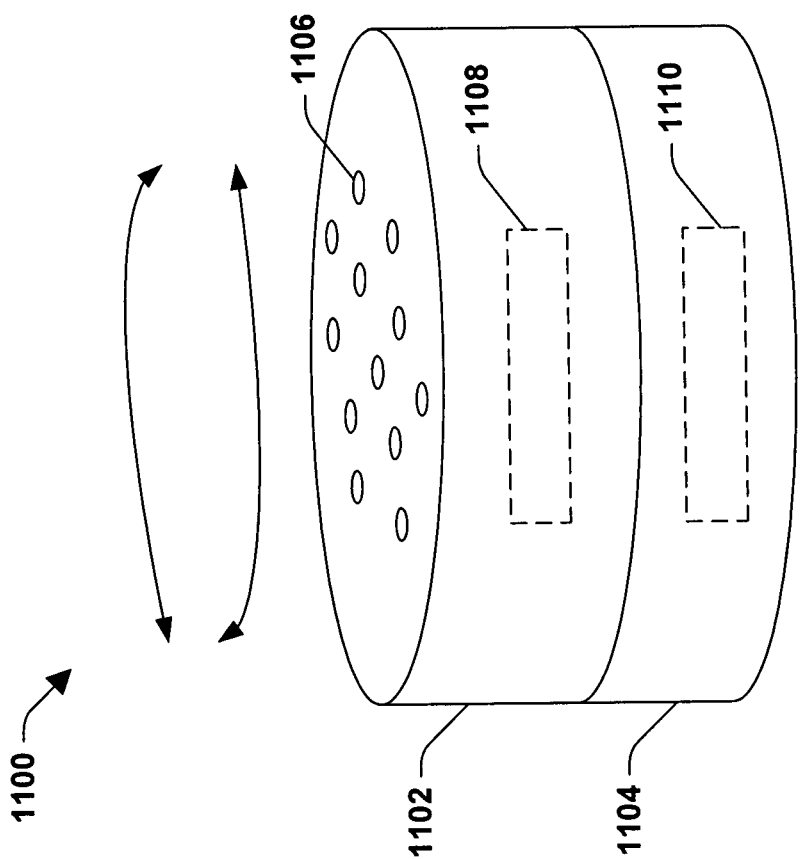
FIG. 11 is an exemplary environment in which the present invention can operate in accordance with an aspect of the present invention.

Now turning to FIG. 11, another exemplary device 1100 that can be employed in connection with practicing the present invention is illustrated. The device includes cylinders 1102 and 1104 that are moveable with respect to one another (e.g., the first cylinder 1102 can be moveable and/or the second cylinder can be moveable). Upon rotating the first cylinder 1102 with respect to the second cylinder 1104, apertures 1106 can be opened to allow fluid to enter/exit the first cylinder 1102. The first cylinder 1102 can thereafter be rotated with respect to the second cylinder 1104 (either in a substantially similar or opposite direction) to facilitate closing the apertures 1106. Opening and closing the apertures enables a sample of fluid to be confined within the first cylinder 1102 and thereafter analyzed. For example, the first cylinder 1102 can include sensing elements 1108, and the second cylinder can comprise electronics 1110 that facilitate analyzing data obtained by the sensing elements 1108. Alternatively, the sensing elements 1108 and electronics 1110 can be integrated.

Figure 12:
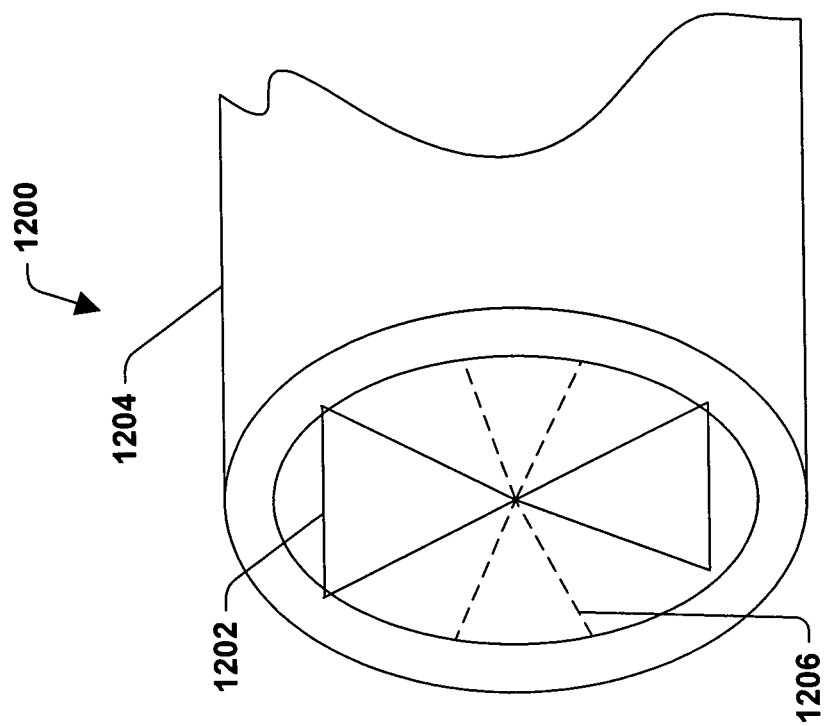
FIG. 12 is an exemplary environment in which the present invention can operate in accordance with an aspect of the present invention.

Referring to FIG. 12, an exemplary probe tip 1200 that facilitates confining a sample of fluid and analyzing such fluid is illustrated. The probe tip 1200 includes covers 1202 that are rotary with respect to a cylindrical casing 1204. The cylindrical casing 1204 comprises slotted openings 1206 that can be covered by the covers 1202. Thus, the covers 1202 can be rotated to enable fluid to flow into and out of the cylindrical casing 1204 via at least partially misaligning the covers 1202 with the slotted openings 1206. Rotating the covers 1202 to cover the slotted openings 1206 prohibits fluid from entering and/or exiting the cylindrical casing. Thus the probe tip 1200 can be employed to confine a sample of fluid within the cylindrical casing 1204, thereby enabling robust analysis of the fluid as discussed herein. Periodically confining disparate samples of fluid within the cylindrical casing 1204 provides for optimal monitoring and maintenance of a main supply of fluid.

Figure 13:
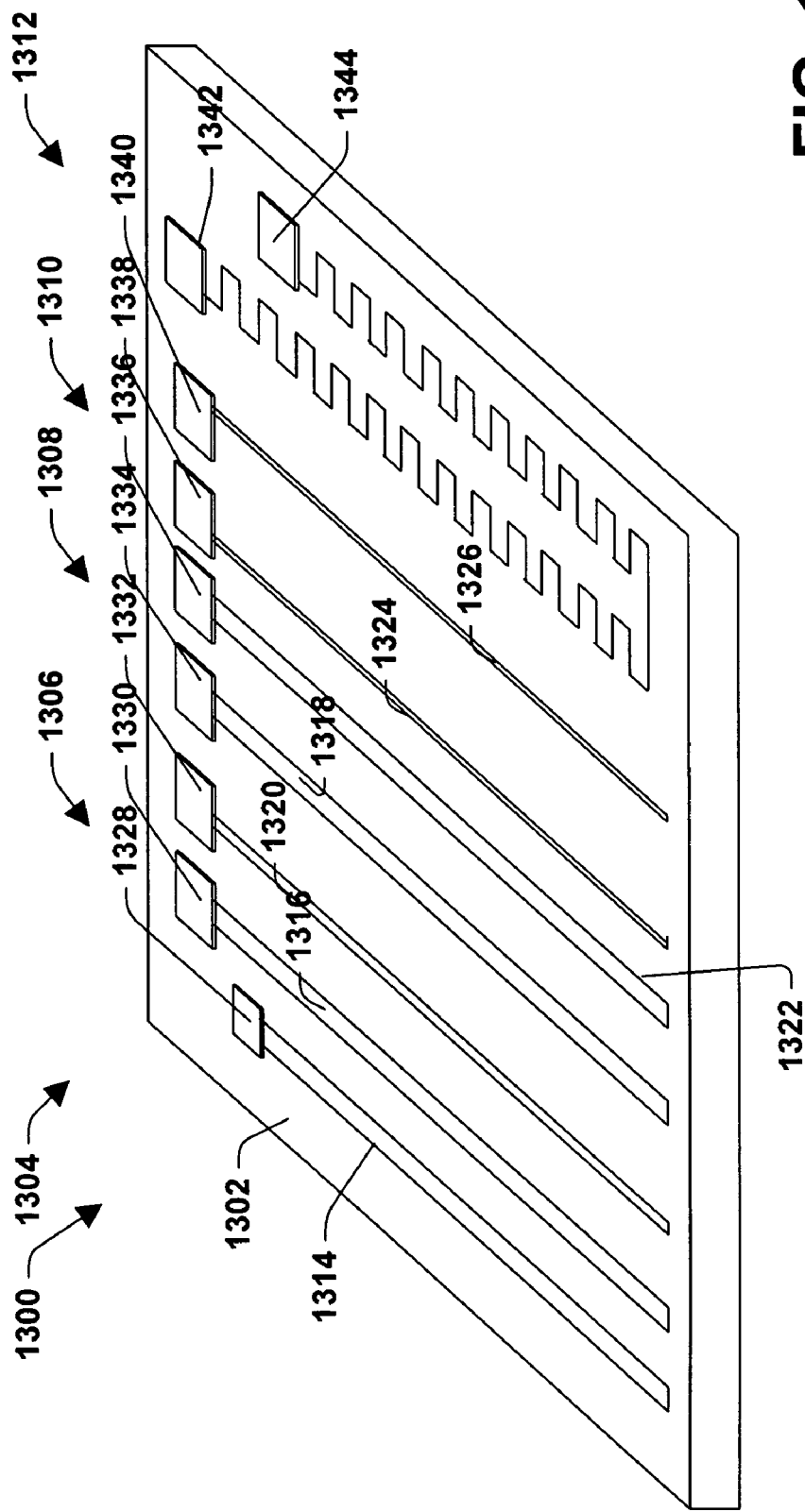
FIG. 13 is an exemplary multi-element sensor that can be utilized in connection with the present invention.

Referring now to FIG. 13, an exemplary micro electromechanical system type (MEMS-type) multi-element fluid sensor 1300 that can be employed in connection with the present invention is illustrated. The present invention affords for in situ monitoring of a variety of fluid parameters via a plurality of sensing devices (elements). A data fusion framework can be associated with the fluid sensor 1300 to facilitate condensing, combining, evaluating and interpreting the various sensed data. The sensor 1300 can be employed in rotating machinery that utilizes fluid as lubrication. In addition, the sensor 1300 can also be applied to measure various parameters of hydraulic fluids and cutting fluids, vehicle fuels (e.g., aircraft, marine, and land-based), food products (e.g., cooking oils), as well as biological fluids. In accordance with one aspect of the present invention, the sensor 1300 can be placed within a casing (not shown) comprising one or more aperture(s) that can be opened and closed. A sample of fluid can thus enter the casing when the aperture(s) are open, and can be confined within the casing when the aperture(s) are closed. The sensor 1300 can then be utilized for real-time in situ measurement, analysis, and maintenance of fluid within machinery. The fluid sensor 1300 includes a semiconductor base 1302 that preferably comprises silicon, however, any suitable material may be employed. Located on the surface of the base 1302 are a plurality of sensing devices 1304 for sensing various parameters of a fluid. More particularly, the sensing devices 1304 include a pH sensor 1306 for sensing pH of the fluid, or the fluid acidity or baseness (TAN, SAN, TBN, etc.). An electrochemical sensor 1308 provides for sensing chemistry of the fluid, including oxidation levels of the fluid. A conductivity sensor 1310 provides for sensing electrical conductivity of the fluid. A temperature sensor 1312 provides for sensing temperature of the fluid.

The pH sensor 1306 includes a reference electrode 1314 comprising any suitable material (e.g., Ag, AgCl) and a pH electrode 1316 comprising any suitable material (e.g., palladium-palladium oxide (Pd—PdO)). The pH sensor 1306 provides for sensing the pH of a lubricant or fluid being analyzed. An exemplary discussion relating to pH sensors is found in "A Pd—PdO Film Potentiometric pH Sensor, by Karagounis et al., IEEE Transactions on Biomedical Engineering, Vol. BME-33, No. 2, February 1986 which is hereby incorporated by reference in its entirety.

The electrochemical sensor 1308 is of a 3-electrode configuration that includes a reference electrode 1318 comprising any suitable material (e.g., Ag, AgCl), a working electrode 1320 (e.g. comprising Ag) and a counter electrode 1322 (e.g., comprising Ag). The chemical sensor 1308 is of a design typically used in conjunction with voltammetric techniques. It is to be appreciated that other suitable sensor designs including a 2-electrode or four electrode electrochemical sensor, may be employed. When either an AC or DC voltammetric signal is applied to the working electrode 1320, a response current is generated between the working electrode 1320 and the counter electrode 1322. The response current signal parameters vary depending upon the electrochemical processes occurring at the surface of the working electrode 1320. The electrochemical processes are a function of the constituent concentrations, and the response current is therefore responsive to these concentrations. The electrochemical sensor is useful for determining the presence of contaminants like water, fuel, glycd, unwanted chemicals, and/or oxidation, for example, in a fluid being analyzed.

Furthermore, the chemical sensor 1308 can be employed to reduce oxidation present in a fluid. Typically, an amount of oxidation present in fluid can be determined via cyclic voltammetric techniques. A voltage is cyclically ramped from a positive voltage to a substantially equivalent negative voltage, and a response current between the working electrode 1320 and the counter electrode 1322 is captured. Characteristic peaks in the current-voltage curve is driven by oxidation and reduction occurring in fluid that is in close proximity to the electrodes 1318, 1320, and 1322. Such an oxidation measurement technique is ineffective in conventional systems, as fluid is flowing and non-static, thus not allowing an oxidation and reduction cycle to complete near the electrodes 1318, 1320, and 1322. Oxidation levels of the fluid, however, can be effectively measured by confining a sample of the fluid in a casing 102 (FIG. 1) comprising the sensor 1300. Moreover, as a sample of fluid is confined, the electrodes 1318, 1320, and 1322 can reverse oxidation in the sample of fluid via performing substantially more reduction on the sample of fluid than oxidation during the voltammetric cycle.

In many cases, lubricating oils and hydraulic fluids are non-polar fluids that exhibit a very weak electro-chemical response. As a result, extraction of a sample is required and the sample is chemically modified via an addition of a solvent or electrolyte. After such addition occurs, a voltammetric cycle can be performed on the sample. Such an approach is not practical for in-line continuous monitoring. However, the present invention enables a small amount of electrolyte or solvent to be added automatically to the confined volume just prior to voltammetric sensor operation, thereby enabling in-line continuous monitoring of oxidation.

An oxidation reaction is not addition of oxygen to compounds in a fluid, but rather a loss of electrons in a fluid compounds. Similarly, a reduction phase of a voltammetric cycle results in a gain of electrons for fluid compounds. Thus a substantially greater voltage signal can be provided for a substantially greater time during a reduction phase when compared to an oxidation phase (e.g., a brief, low voltage signal will be provided for the oxidation phase). The increase amount of time in the reduction phase reduces oxidation present in fluid compounds. Moreover, the electrodes 1318, 1320, and 1322 can be constructed to enable greater amounts of voltage(s) than typical electrodes, and can further be constructed to provide a large surface area to facilitate reduction of a larger sample of fluid. While a single chemical sensor 1308 is illustrated, it is to be understood that the present invention contemplates a utilization of an array of electrodes 1318, 1320, and 1322 that can be alternatively selected to lengthen useful life of the chemical sensor 1308. Thus the chemical sensor 1308 can be employed to impede further degradation of a fluid within machinery, thus lessening probability of human error that can occur in maintaining machinery, as well as reducing cost of replacing fluid. Furthermore, the sensing capabilities of the chemical sensor 1308 together with the fluid maintenance capabilities of the chemical sensor 1308 can be utilized to create a closed-loop control system (e.g., oxidation levels are continuously sensed, and a control system utilizes the sensed oxidation levels to determine voltages to apply to electrodes 1318, 1320, and 1322).

In accordance with another aspect of the present invention, micro-electronic magnetic structures can be fabricated together with the electrodes 1318, 1320, and 1322. Providing energy to the micro-electronic magnetic structures results in attraction of to ferrous metallic particles from the fluid to the magnetic structures. Presence of the magnetic field generated by the magnetic structures prevents such ferrous metallic particles from flowing freely in a fluid and thereby mitigates occurrences of such particles from contacting sensitive surfaces in machinery (e.g., a bearing raceway). For example, the ferrous particles can be bound to a sensor electrode with a plating-type operation. An amount of ferrous materials attracted can be measured with any suitable techniques that include conductivity between several sensor electrodes, plating energy, or capacitive or dielectric strength between surfaces.

The conductivity sensor 1310 is of a two-electrode design, however, it is to be appreciated that other configurations (e.g., four electrode) may be employed. In the preferred embodiment, the two electrodes (1324, 1326) comprise gold, however, any suitable metal or material may be employed. Two and four electrode conductivity sensors are well known and thus further discussion related thereto is omitted for sake of brevity. Knowledge of the conductivity is also useful for determining if metal wear and/or water is contaminating a fluid, for example.

The temperature sensor 1312 provides for determining the temperature of the fluid being analyzed, and is preferably formed from platinum, however, it is to be appreciated that any material (e.g., gold) suitable for carrying out the present invention may be employed. The temperature sensor 1312 is patterned on the base 1302 in accordance with a predetermined length, width and surface area. Therefore, by knowing the surface area of the temperature detector 1312 and the material of which it is made, a temperature of a fluid to which the temperature sensor 1312 is exposed may be determined based on the electrical conductivity of the temperature detector 1312. Knowledge of fluid temperature is useful in interpreting the health state of the fluid being analyzed because certain fluid parameters (e.g. viscosity) are a function of fluid temperature. Furthermore, the rate of fluid breakdown or additive depletion is also a function of temperature. Therefore, predicting the remaining useful life of a fluid also requires temperature measurement.

In accordance with one aspect of the present invention, the temperature sensor 1312 can be a resistance temperature sensor, thereby enabling the temperature sensor 1312 to operate as a heater. As a current flows between the electrodes 1342 and 1344, the electrical resistance will cause the metallic interconnect and/or wire to heat up along with anything proximate to the metallic interconnect. The sensor element 1312 can effectively heat up and then sense a temperature of a small confined fluid sample. Such a process enables testing of a fluid at various known, controlled temperatures. This useful technique is not practical for unconfined fluid sampling due to potential damage to machinery and fluid that can result from excessive temperature, potential safety and process problems by operating equipment at elevated temperatures, and an amount of energy required to heat large volumes of fluid in a thermally conductive system. Therefore, it may be desirable to fabricate multiple temperature sensor elements 1312 on a single device or substrate. A plurality of temperature sensor element 1312 can be readily used for closed-loop feedback control of heat emitted by such temperature sensor elements to maintain precise control of temperature of the confined fluid. Acquiring data from other sensor elements at a controlled fluid temperature can significantly improve consistency of sensed parameters and enhance analysis capabilities regarding such parameters. It is to be noted that a casing that encloses the sensor 1300 can be constructed of thermally non-conductive materials to aid in controlling temperature of a confined fluid.

Each fluid parameter sensor (e.g. pH sensor 1306, electrochemical sensor 1308, conductivity sensor 1310, temperature sensor 1312) has respective sets of contact pads 1328–1344 that provide for easy coupling to the respective sensors. The fluid sensor 1300 is small having a square area of approximately 4 mm. Accordingly, the fluid sensor 1300 is desirable for use in applications where space is at a premium but where accuracy, reliability, and sensitivity of measured data are also at a premium. Furthermore, because the fluid sensor 1300 is fabricated in accordance with integrated circuit-like fabrication techniques, large batches of the fluid sensors 1300 may be easily and efficiently produced with good production yields, using conventional wafer fabrication facilities.

Furthermore, it is to be understood that some sensing devices 1304 may be omitted from the fluid sensor 1300 and/or different types of sensing devices (e.g., pressure sensor, IR sensor, light sensor, density sensor, light transmission sensor, shear sensor) may be incorporated into the fluid sensor 1300. One, some or all of the sensing devices 1304 may be replicated "n" number of times (wherein "n" is an integer) on a single fluid sensor 1300. Such an embodiment may provide for increased reliability because if one particular sensing device failed there would be like sensing devices serving as backups. Multiple sensing devices of the same type on a single fluid sensor 1300 may also afford for increased accuracy as a result of improved signal to noise ratio. The multiple versions of the same sensing element type may span a wide range of sizes, ratios, etc., each of which has a range of optimal sensing accuracy. Together these sensor elements 1304 provide for substantial accuracy over a wide range of parameter values. The replicated sensing devices 1304 may also improve dynamic range of the fluid sensor 1300 as well as versatility (e.g., the fluid sensor 1300 may be employed on a wide range of materials and/or fluids). Such an embodiment may also have enhanced integrity because it may be able to sense if a particular sensing device 1304 has failed or to identify the type of contaminant (e.g., engine coolant, transmission fluid, gear oil, . . . ).

Figure 14:
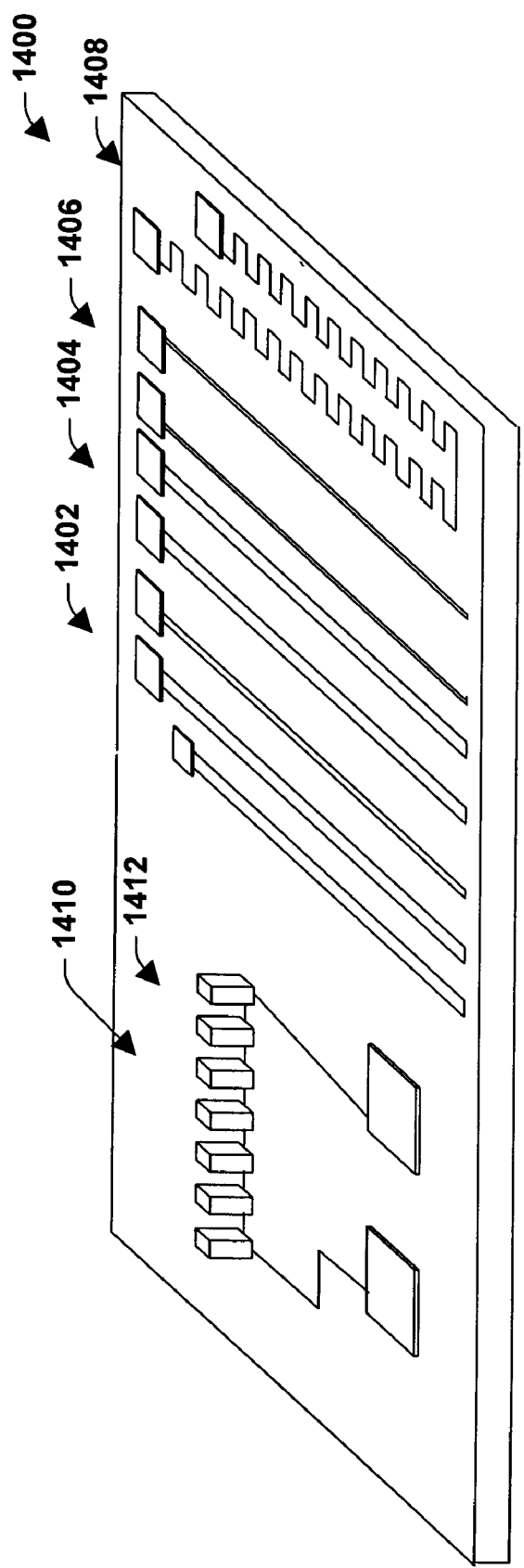
FIG. 14 is an exemplary multi-element sensor that can be utilized in connection with the present invention.

FIG. 14 illustrates another exemplary multi-element sensor 1400 that can be utilized in connection with the present invention. The multi-element sensor 1400 includes a pH sensor 1402, an electrochemical sensor 1404, a conductivity sensor 1406, a temperature sensor 1408, and a viscosity sensor 1410. The pH sensor 1402, the electrochemical sensor 1404, the conductivity sensor 1406, and the temperature sensor 1408 are essentially the same as that described in connection with FIG. 6 and therefore further discussion related thereto is omitted for sake of brevity. The viscosity sensor 1410 provides for sensing the viscosity of a fluid being analyzed. In short, the viscosity sensor 1410 works in conjunction with the temperature sensor 1408 to facilitate analyzing viscosity of the fluid being analyzed.

The viscosity sensor 1410 includes a plurality (e.g., array) of finger-like elements (e.g., cilia) 1412 which are plated with an electrically conductive material. The finger-like elements 1412 extend perpendicularly from a surface 1414 of the sensor, and the sensor 1410 functions based on a phenomena that a dissipative or damping force that resists the motion of the energized finger-like elements 1412 results in an increased power demand to maintain oscillation of the finger-like elements 1412 at a particular frequency. A fluid of high viscosity will exert a greater damping force on the oscillating finger-like elements 1412 than a fluid of lower viscosity. As a result, more power is required to maintain oscillation of the finger-like elements 1412 at a particular frequency in a high viscosity fluid than a fluid of lower viscosity. Thus, the viscosity of a fluid may be determined via the micro viscosity sensor 1410 of the present invention by monitoring the power required to oscillate the finger-like elements 1412 at a particular frequency and/or range of frequencies. Since the viscosity of a fluid is also a function of fluid temperature (e.g., typically, the higher the fluid temperature the lower the fluid viscosity), the present invention also employs the temperature detector 1408 to correlate the temperature of the lubricant or fluid with the aforementioned power requirements to accurately interpret lubricant or fluid viscosity. Varying temperature enables determination of accuracy of viscosity measurements, as well as presence of contaminants, sensor failure, etc. As described infra, the temperature of a fluid can be varied, which facilitate generation of a complete viscosity curve that can be employed in connection with fluid analysis. Furthermore, in several fluids (non-Newtonian fluids) viscosity varies with shear rate. Thus a MEMs viscometer can be operated at disparate frequencies to further analyze non-Newtonian and other similar fluids. Moreover, entrapping a small sample of fluid in a casing, and thereafter moving the casing (e.g., vibrating the container) enables determination of fluid density (an extremely important fluid parameter for fluid analysis) based upon energy required for movement. Determination of density facilitates determining a kinetic viscosity from the absolute viscosity measured with the sensor 1410. A more detailed discussion relating to the operation and fabrication of such a viscosity sensor is found in U.S. Pat. No. 6,023,961, entitled MICRO-VISCOSITY SENSOR AND LUBRICATION ANALYSIS SYSTEM EMPLOYING THE SAME, which as mentioned above is hereby incorporated by reference in its entirety.

Figure 15:
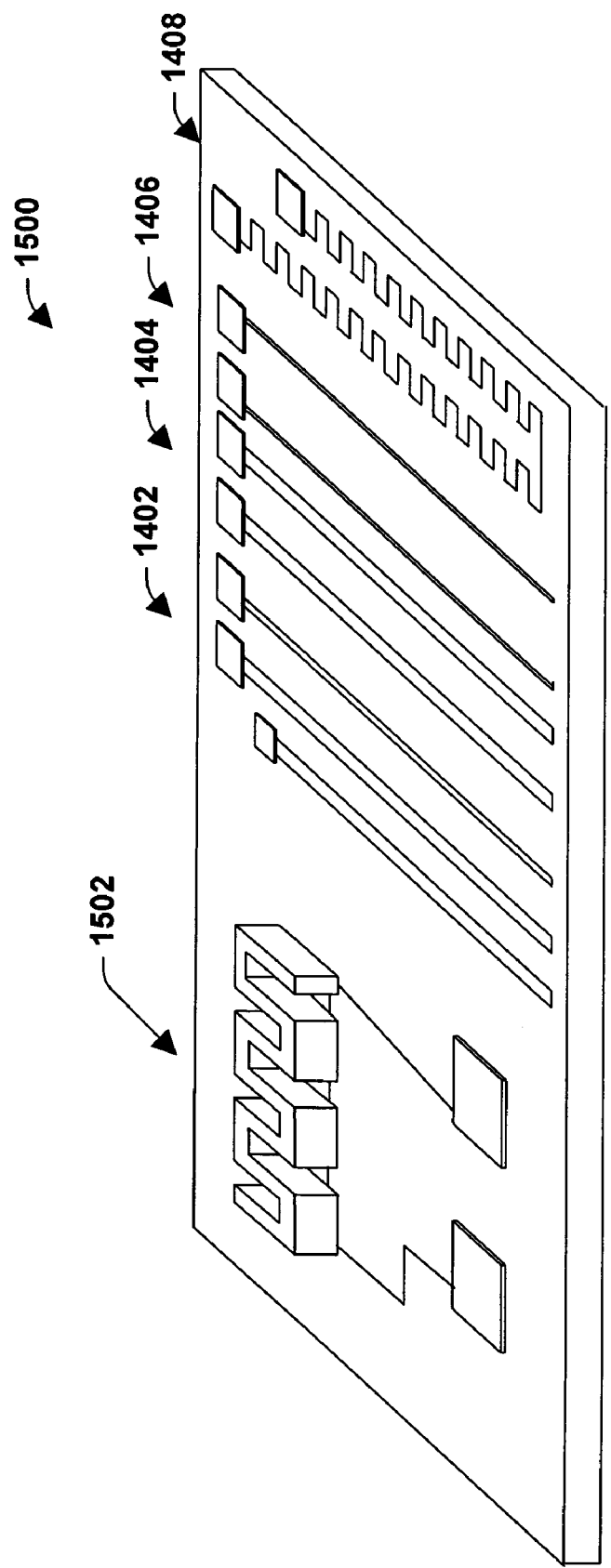
FIG. 15 is an exemplary multi-element sensor that can be utilized in connection with the present invention.

Referring now to FIG. 15, an exemplary multi-element sensor 1500 that can be employed in connection with the present invention is illustrated. FIG. 15 includes several components that are substantially similar to components illustrated in FIG. 14 and described above, therefore discussion pertaining to such components is omitted for sake of brevity. Like reference numerals are utilized to refer to like elements. The multi-element sensor includes a viscosity sensor 1502 that utilizes a comb-like structure to determine viscosity, which operates in a similar manner as the viscosity sensor described above. The multi-element sensor 1500 is displayed to illustrate that a plurality of disparate viscosity sensors are contemplated and intended to fall within the scope of the hereto-appended claims.

Figure 16:
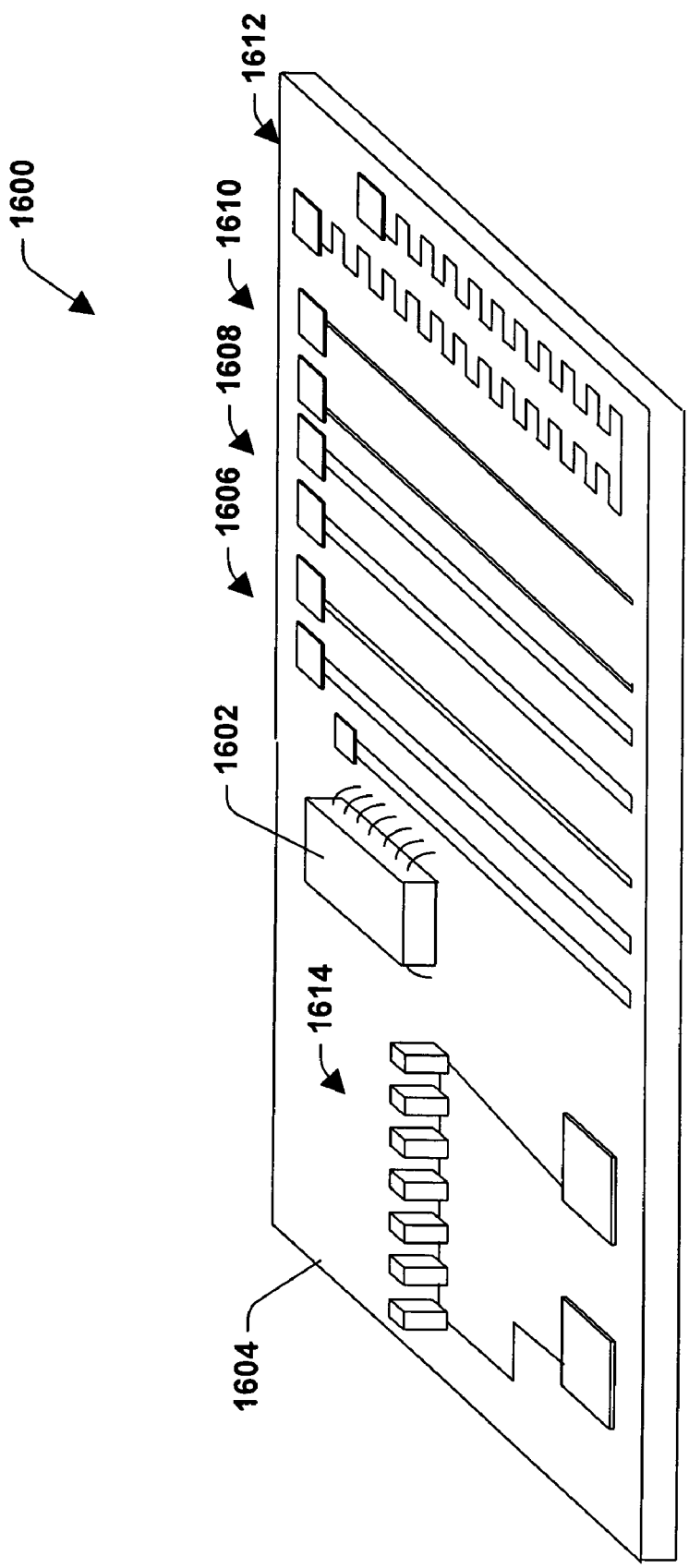
FIG. 16 is an exemplary multi-element sensor that can be utilized in connection with the present invention.

FIG. 16 illustrates another exemplary multi-element sensor 1600 that can be employed in connection with the present invention. The multi-element sensor 1600 also includes a processor 1602 integrated on a semiconductor surface 1604. While the processor is illustrated as a single device, it is understood that multiple devices that function together as a processor are contemplated and are intended to fall within the scope of the hereto-appended claims. For example, the processor can include an analog section and a digital/computational section. The analog section can comprise a plurality of analog filters, comparators, amplifiers, and/or signal generators as well as other analog functions for each sensor element. A/D and D/A logic function in the processor 1602 can be within a standard processor chip or implemented as a customized logic element, wherein such functions can be customized for performance, size, environment and power requirements of a particular sensor. The digital and analog elements can be integrated into a single chip, or alternatively distributed over multiple devices. For instance, the processor 1602 includes devices such as FPGA devices, ASIC devices, or fully custom integrated circuits. The processor 1602 can receive measurements obtained by a plurality of sensing elements, such as a pH sensor 1606, an electrochemical sensor 1608, a conductivity sensor 1610, a temperature sensor 1612, and a viscosity sensor 1614. The processor 1602 is employed to carry out general operations of the multi-element sensor 1600 including data fusion in accordance with an exemplary data fusion framework described in U.S. Pat. No. 6,286,363. The processor 1602 can be any of a plurality of suitable processors, such as for example: CPU die or processor/logic/storage bonded (flip chip) to the sensor substrate—the sensor elements may be wire bonded to processor I/O connection points. The manner in which the processor 1602 can be programmed to carry out the functions relating to the present invention will be readily apparent to those having ordinary skill in the art based on the description provided herein and thus further discussion related thereto is omitted for sake of brevity. Thus, the multi-element sensor 1600 provides for a substantially autonomous fluid measurement, analysis, and automatic maintenance system system. The multi-element sensor 1600 can provide for performing fluid analyzer functions as well as affording for self-diagnosis. The multi-element sensor 1600 may also be able to verify that it is in a feasible operating regime.

Figure 17:
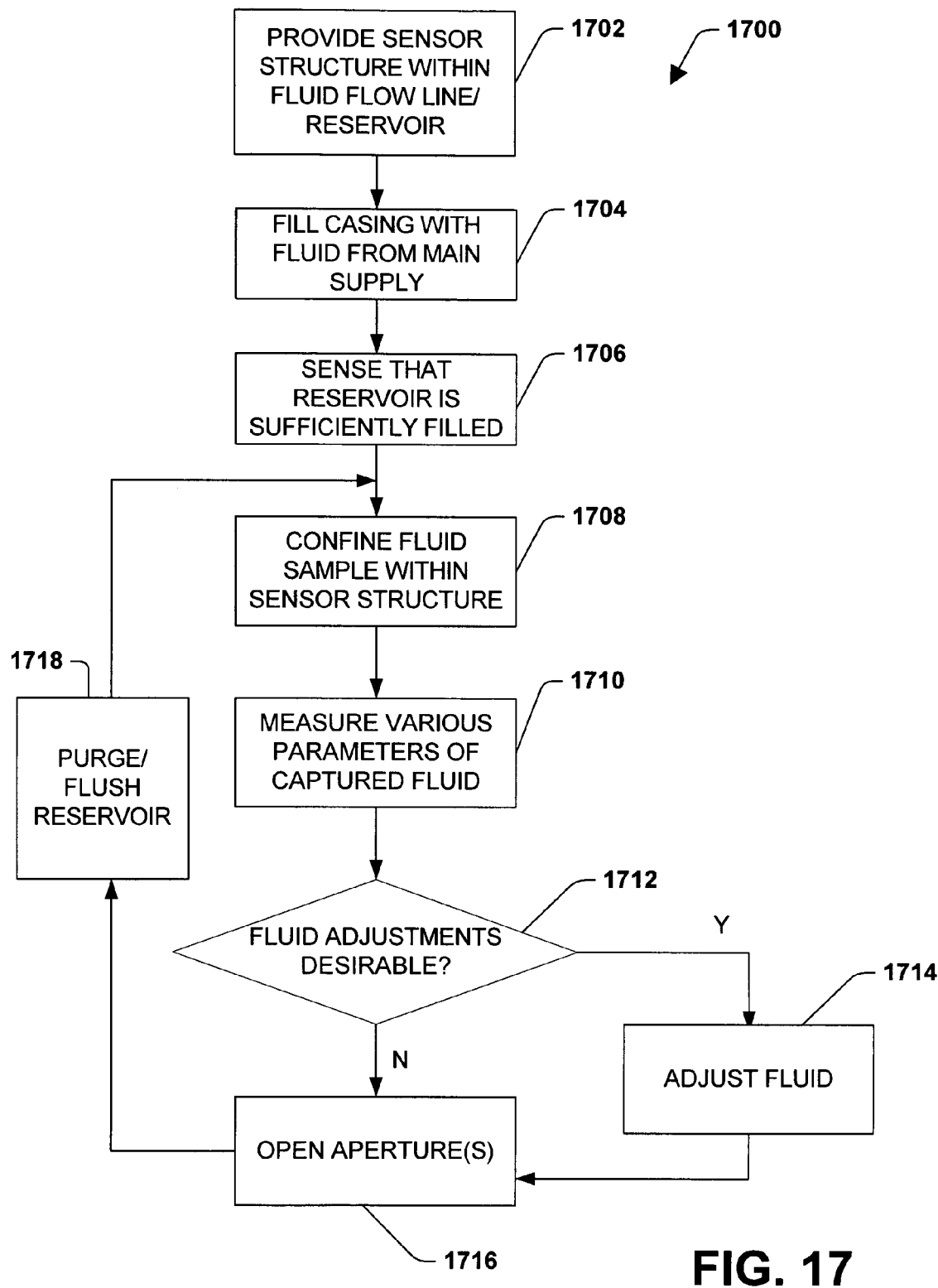
FIG. 17 is a representative flow diagram that illustrates a methodology that facilitates measurement, analysis, and automatic maintenance of fluids within machinery in accordance with one aspect of the present invention.

Turning now to FIG. 17, a methodology 1700 for measuring, analyzing, and automatically maintaining fluid within a machine is illustrated. While, for purposes of simplicity of explanation, the methodology 1700 is shown and described as a series of acts, it is to be understood and appreciated that the present invention is not limited by the order of acts, as some acts may, in accordance with the present invention, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the present invention.

At 1702, a sensing structure comprising a multi-element sensor is provided within a fluid flow line, pump, valve, filter, fluid reservoir, and or other component within a fluid system. In accordance with one aspect of the present invention, the structure can be a probe tip mountable in machinery. The probe tip can comprise one or more aperture(s) that can be opened and closed utilizing any suitable means. For instance, an actuator can be provided to open and/or close the aperture(s). When the aperture(s) are open, fluid from the flow line or reservoir can enter the probe tip. The probe tip can include a reservoir, wherein upon fluid from the flow line filling the reservoir, such fluid contacts one or more elements of the multi-element sensor. The probe tip can also include a power supply, a processor, a screen to prevent contaminants from entering and/or exiting the probe tip, displays, LEDs, wireless or hardline communications devices, and other suitable elements related to measurement, analysis, and maintenance of fluid. At 1704, the sensor structure is filled with fluid from a main supply of fluid. For example, apertures can be opened to facilitate filling the sensor structure with fluid from the main supply. At 1706, a sensor is provided that senses when the sensor structure is substantially filled with fluid. At 1708, fluid contained by the sensing structure (e.g., fluid that entered the sensing structure through one or more open aperture(s)) is confined within the sensing structure via closing the aperture(s). The aperture(s) are closed by one or more actuators, MEMs valves, or other suitable mechanisms that provide mechanical closing of aperture(s). Additionally, a sensor can be employed to determine when fluid has reached a particular level, thereby enabling the actuator to close. Furthermore, a sensor can determine whether the actuators are sealed. Moreover, an area in which the fluid will be confined can be pre-heated prior to enabling fluid to enter the reservoir. In accordance with one aspect of the present invention, the probe tip can include an outer cylinder, wherein upon an actuator rotating the outer cylinder the aperture(s) are closed, thereby confining fluid within the probe tip. As fluid fills the sensing structure (e.g., the probe tip), the fluid contacts the sensors within the sensing structure.

At 1710, multi-element sensor(s) obtain measurements of parameters of the confined fluid. For instance, the multi-element sensor(s) can measure pH, temperature, conductivity, chemistry, viscosity, and any other suitable parameter relating to fluids within machinery. Moreover, if the aperture(s) are opened and/or closed via rotating an outer cylinder within the probe tip, an amount of energy required to rotate the cylinder can be indicative of viscosity of the fluid. The sensed parameters can then be received by a control component, or alternatively be subject to data fusion techniques to facilitate robust analysis of the fluid.

At 1712, a determination is made regarding whether measured parameters indicate that fluid within machinery requires modification and/or whether alteration of machine operation is desirable. For example, given a temperature, viscosity, and oxidation level, it can be determined that anti-oxidants can be added to the fluid to prolong useful life of such fluid. If fluid adjustments are desirable, at 1714 the fluid is adjusted. Adjustments can be made first to a confined fluid to confirm alterations and amount of fluid/additive to alter within a main fluid supply. For instance, a controller can be employed to facilitate maintenance of fluid upon reception of various parameters relating to the fluid (e.g., the controller can cause a fluid and/or additive reservoir to release fluid and/or chemical additives into a fluid flow line and/or reservoir within a machine). Alternatively, the controller can effectively alter operation of a rotating machine if such alteration would extend useful life of fluid and/or avoid damage to machinery. For example, speed, load, elevation, and/or procedure can be controlled to extend useful life of a fluid and/or prevent damage. In particular, alterations can be made regarding speed of shift gears, rotor pitch can be limited, resonant frequencies can be avoided based on sensed fluid conditions, etc. In accordance with another aspect of the present invention, oxidation levels within the fluid confined by the sensing structure can be reduced via a modified cyclical voltammetric technique. For example, a substantially higher voltage can be applied for a substantially longer period of time during a reduction phase as compared to an oxidation phase. Such technique facilitates a reduction of electrons, and thus effectively reduces oxidation present within the fluid confined by the sensing structure.

At 1716, the aperture(s) are reopened and fluid is released from the sensing structure and into a fluid flow line and/or fluid reservoir within machinery. A flushing mechanism can also be provided at 1718 to remove substantially all fluid within the sensing structure, as well as remove all contaminants that are captured by screens. Upon releasing the fluid, the aperture(s) can remain open to obtain another sample of fluid for testing purposes. Such regular testing of small samples of fluid facilitates robust measurement, analysis, and/or automatic maintenance of fluid within machinery.

Figure 18:
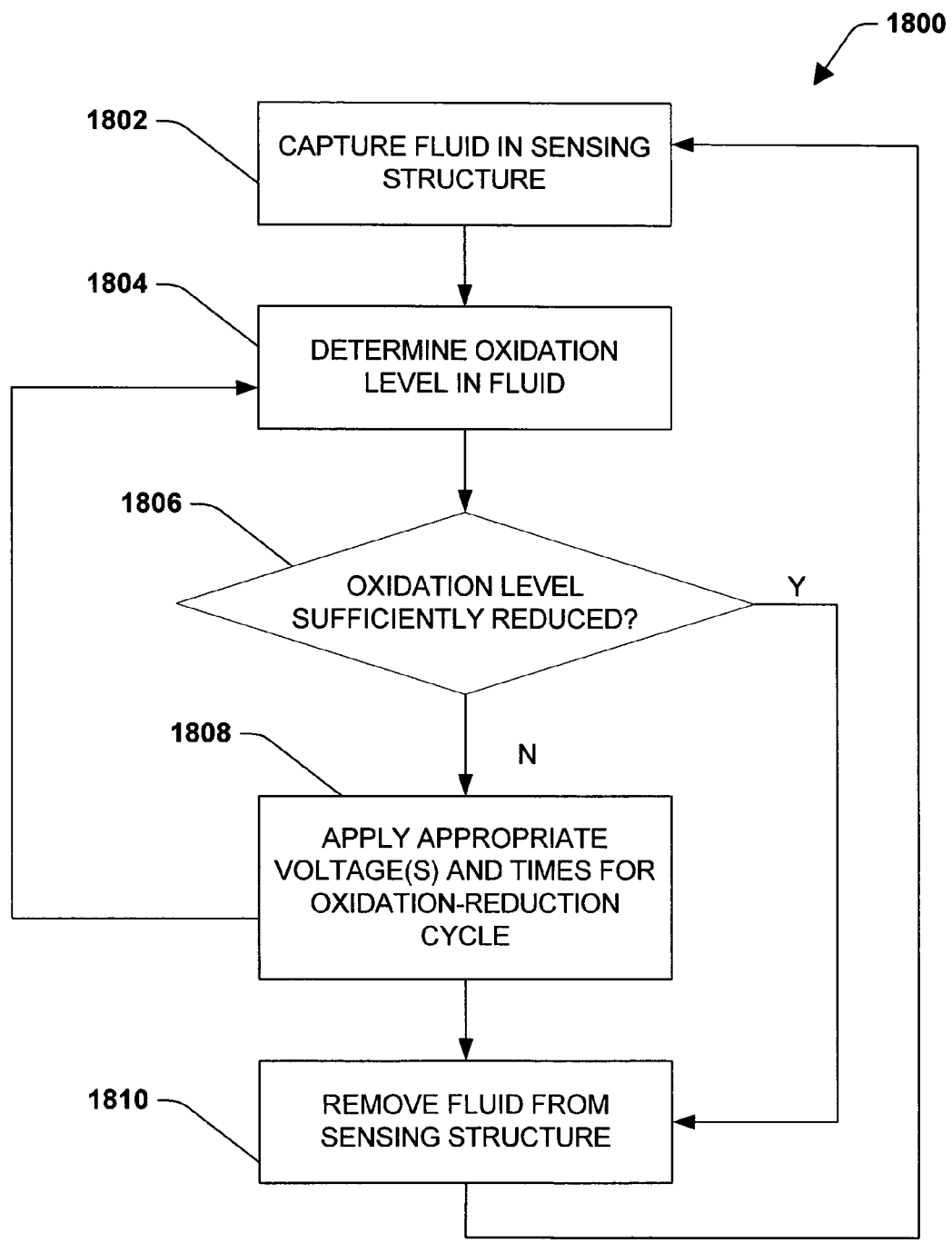
FIG. 18 is a representative flow diagram that illustrates a methodology that facilitates automatic reduction of oxidation levels of fluid within machinery in accordance with an aspect of the present invention.

Turning now to FIG. 18, a methodology 1800 for automatically reducing oxidation levels within a sample of fluid is illustrated. At 1802, fluid is captured in a sensing structure. The sensing structure can be a probe tip comprising one or more multi-element fluid sensor(s), wherein the probe tip has a plurality of aperture(s). The aperture(s) can be opened to allow fluid to flow into the probe tip and contact the multi-element sensor(s), and thereafter the aperture(s) can be closed by an actuator or MEMs valve to confine a sample of the fluid within the probe tip. At 1804, an oxidation level in fluid is determined. In accordance with one aspect of the present invention, a three-electrode sensor can be employed to measure an oxidation level in the sample of fluid. A cyclically ramped voltage is applied across a working electrode and a reference electrode, thereby inducing a current in the counter electrode. The voltage-current curve can then be utilized to determine oxidation levels present in the sample of fluid.

At 1806, a determination is made regarding whether the oxidation level of the fluid is sufficiently reduced. If the oxidation level is not sufficiently reduced, at 1808 appropriate voltage(s) can be applied to the electrodes to facilitate a desirable amount of reduction in the sample of fluid. Such reduction of oxidation can be achieved by delivering substantially greater voltages for substantially greater times during a reduction phase as compared to an oxidation phase. Moreover, as the three electrodes can both measure oxidation and reduce oxidation in a fluid, a closed-loop control system can be easily implemented. Reducing oxidation in a fluid extends useful life of the fluid, thus reducing cost for replacing the fluid as well as reducing probability of human error when maintaining the fluid. Moreover, the oxidation level can be continually checked and corrected until the oxidation level is sufficiently reduced. At 1810, the sample of fluid is removed form the sensing structure (e.g., aperture(s) are opened to allow release of the fluid into a fluid flow line and/or reservoir within a machine). Upon removal of the fluid, a disparate sample can be captured and the methodology 1800 can be regularly repeated. Furthermore, confined fluid can be altered (e.g., reduce oxidation level), and an amount of time and/or power required for such alteration can be recorded, which provides an indication of a state of fluid additives (e.g., antioxidants) or activity or energy required to effect a large fluid reservoir within a system.

Figure 19:
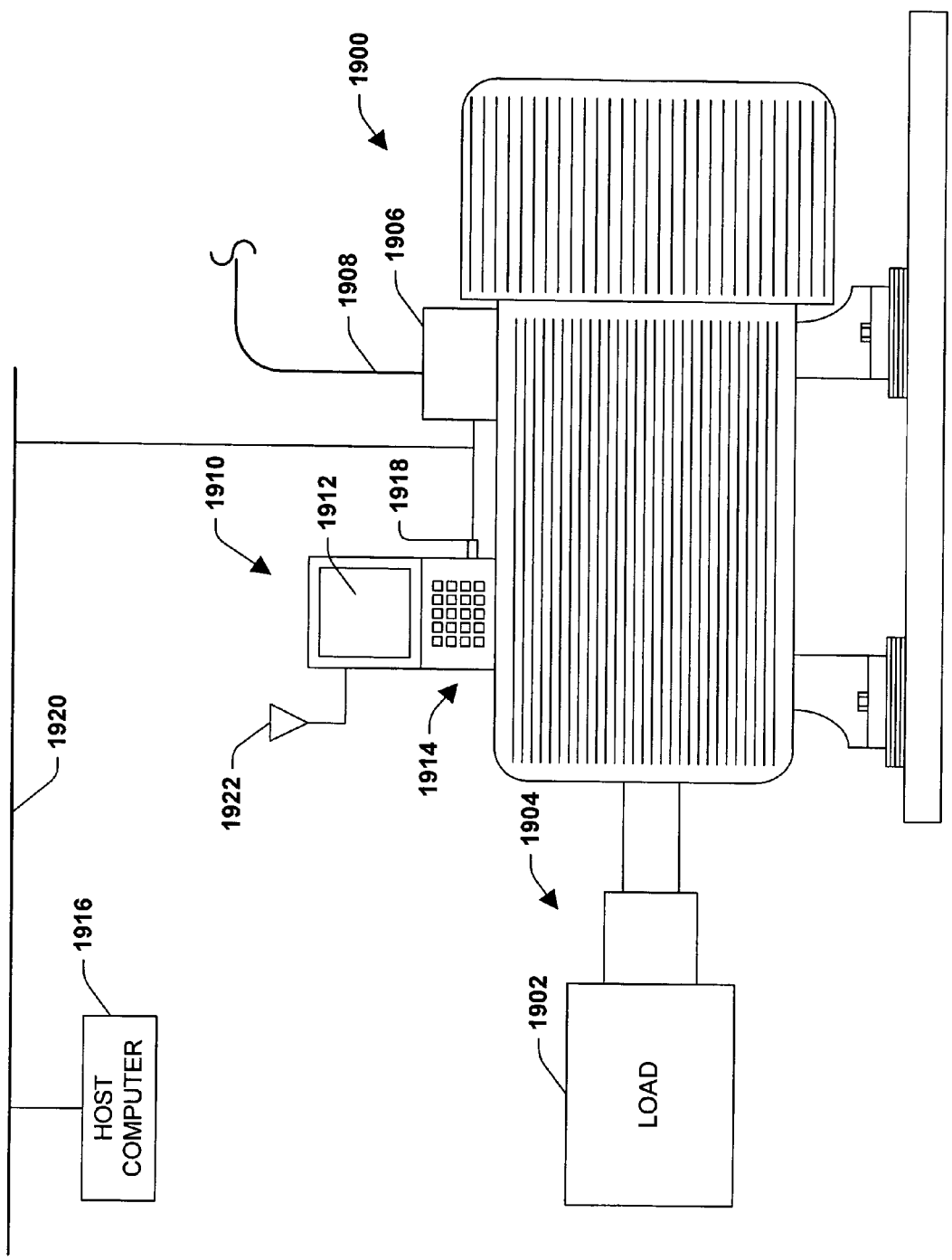
FIG. 19 is an exemplary environment in which the present invention can be employed.

In order to provide context for the present invention, FIG. 19 illustrates an exemplary environment in which the present invention may be employed. A three-phase AC induction motor 1900 is depicted driving a load 1902 through a shaft coupling 1904. The motor 1900 includes a junction box 1906 for receiving conductors from power lines via a conduit 1908, which are tied to power supply lines (not shown) of the motor 1900. The motor 1900 is AC powered and operates at an AC power line frequency of 60 Hz. However, it is appreciated that different line frequencies (e.g., 50 Hz) may be employed. Coupled to the motor 1900 is a fluid analyzer 1910 which as will be discussed in greater detail below provides for receiving and processing data relating to the health of fluid employed by the motor 1900. In accordance with one aspect of the present invention, the fluid analyzer 1910 facilitates analysis of lubrication data from a plurality of multi-element sensors. Moreover, multi-element fluid sensors can communicate directly to the fluid analyzer 1910 via a wireless and/or wireline connection The fluid analyzer 1910 includes a display 1912 for displaying to an operator information relating to the health of the fluid. It is to be appreciated that the fluid analyzer 1910 may also perform other functions relating to determining the health of the motor 1900 (e.g., current signature analysis, vibration analysis, etc.). The fluid analyzer 1910 further includes an operator input device 1914 in the form of a key pad which enables a user to enter data, information, function commands, etc. as is conventional. For example, the user may input information relating to fluid type via the keypad 1914 for subsequent transmission to a host computer 1916. In addition, the keypad 1914 may include up and down cursor keys for controlling a cursor that may be shown on the display 1912. The fluid analyzer 1910 includes a communications port 1918 for interfacing the fluid analyzer 1910 with the fluid sensor 1200 (FIG. 12) and the host computer 1916 via a suitable communications link. Alternatively, it is to be understood that the host computer 1916 can receive data directly from one or more fluid sensors via a wireless and/or wireline connection.

According to an embodiment of the present invention, the lubrication analyzer 1910 is part of a communication system including a network backbone 1920. The network backbone 1920 may be a hardwired data communication path made of twisted pair cable, shielded coaxial cable or fiber optic cable, for example, or may be wireless or partially wireless in nature. Thus the fluid analyzer 1910 can be provided with a wireless receiver/transmitter 1922 for receiving and/or relaying data pertinent to fluid analysis. Information can also be transmitted via the network backbone 1920 between the host computer 1916 and the lubrication analyzer 1910. The communication link preferably adheres to the RS232C or DeviceNet standard for communicating command and parameter information. However, any communication link suitable for carrying out the present invention may be employed. In accordance with one aspect of the present invention, all processing, including signal generation/signal processing operations discussed with respect to FIG. 19, can be performed and integrated within a sensor housing (e.g., casing 102 as illustrated in FIG. 1). Alternatively, all processing can be performed remote from the sensor in the host computer 1916. Furthermore, a portion of processing can be performed within a sensor housing (e.g., signal generation) while a portion or processing can be performed externally. It is also to be understood that a device employed to practice the present invention can be positioned in a plurality of disparate locations. For example, a sensing device can be located within bearings of a motor, within oil in a load device (e.g., pump interior), as well as within a connected gear box.

Figure 20:
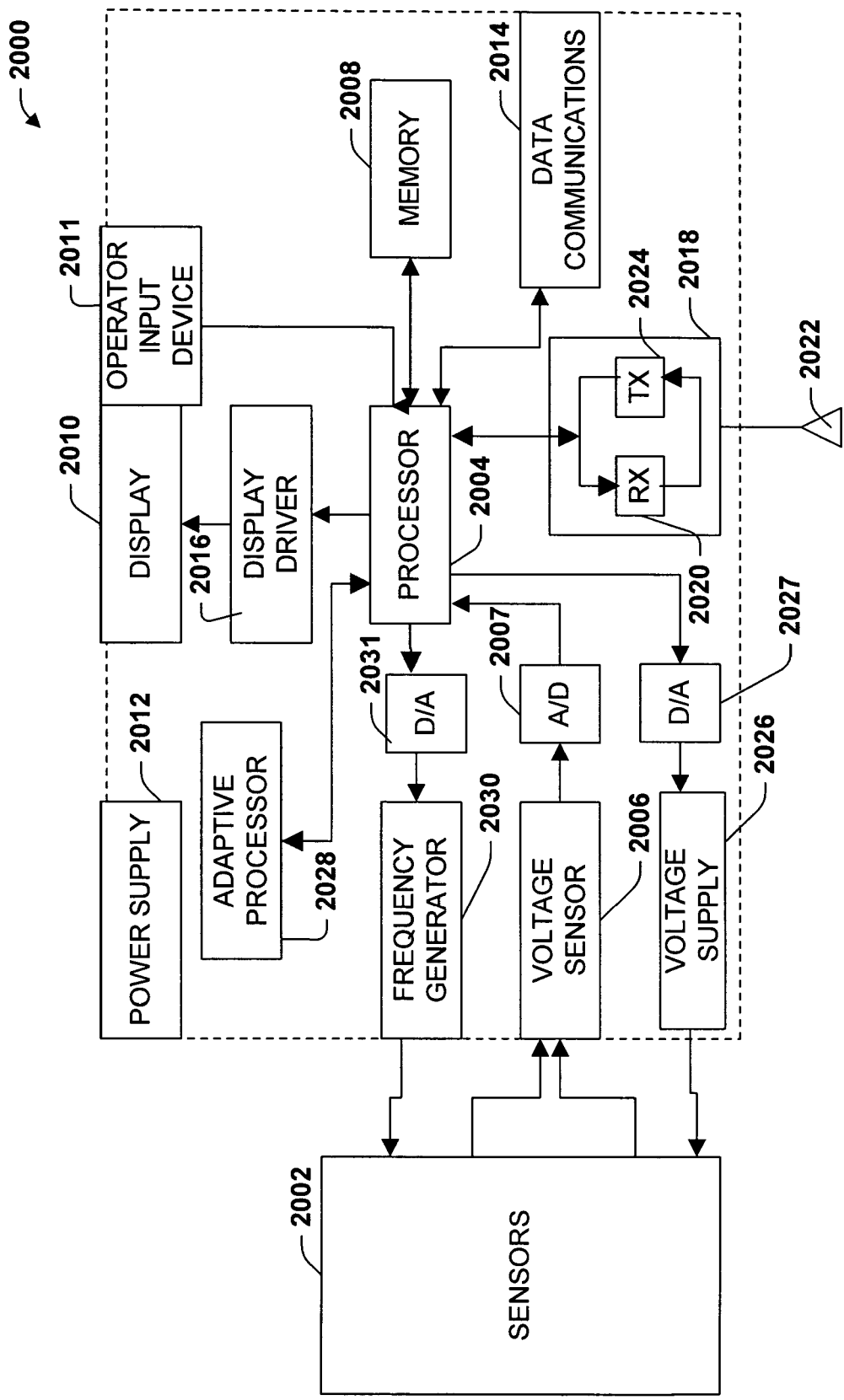
FIG. 20 is an exemplary schematic in accordance with one aspect of the present invention.

Referring now in to FIG. 20, a schematic representation of the present invention is shown according to one particular aspect of the present invention, wherein a fluid analyzer 2000 is integrated with the fluid sensor 2002. However, it will be appreciated from the discussion herein that the fluid analyzer 2000 may be located remotely from the motor 1900 (FIG. 19). Furthermore, it is to be appreciated that the host computer may serve to carry out substantially all of the functions described herein performed by the fluid analyzer 2000. It is also to be appreciated that in accordance with another specific aspect of the present invention, the fluid analyzer 2000 (absent certain components) may be integrated onto a semiconductor chip with the fluid sensor 2002. In accordance with another specific embodiment, the fluid analyzer 2000 may be completely integrated within the motor 1900 (e.g., in an intelligent motor), a gearbox, pump, filter, drain or a bearing, for example. It is to be further appreciated that the sensor 2002 can comprise various portions in connection with measuring a plurality of parameters of a fluid. For instance, the sensor 2002 can include a digital/calculation portion as well as analog circuitry. Furthermore, additional circuitry can be provided to interface the sensors 2002 with circuitry within the fluid analyzer (e.g., amplifiers, filters, . . . ). Moreover, a plurality of sensors can be connected to the fluid analyzer 2000 (e.g., several multi-element sensors can be connected to a single fluid analyzer).

In the preferred embodiment, the fluid analyzer 2000 includes a housing that is suitably shielded to protect the fluid analyzer 2000 from whatever environment (e.g., dust, moisture, heat, vibration, lubrication) the motor 1900 is working in. Additionally, the interior of the fluid analyzer 2000 may be suitably insulated with thermal insulation between the motor and the fluid analyzer 2000 so as to protect it from heat generated by the motor 1900. The fluid sensor 2002 can include a pH sensor, an electrochemical sensor, a conductivity sensor, a temperature sensor, a viscosity sensor, ferrous contaminant sensor, corrosion sensor, and any other suitable sensor that can be employed to measure various parameters of a fluid within a machine. The fluid sensor 2002 is operatively coupled to a processor 2004 of the fluid analyzer 2000 via respective analog to digital (A/D) converters 136 which convert the analog signals output from the fluid sensor 2002 to digital form for processing by the processor 2004.

A sensor for measuring temperature (not shown) varies in electrical conductivity depending on the temperature of the fluid. Accordingly, the temperature of the fluid can be determined from the output of a voltage sensor 2006 which can be coupled to a temperature detector because the output voltage will vary in correspondence with the fluid temperature. The voltage sensor can communicate with the processor 2004 via a A/D converter 2007. The following table illustrates the analytic relationship between fluid viscosity and fluid temperature, which can be monitored via the conductivity of a temperature detector.

| CONDUCTIVITY OF TEMP. DETECTOR | FLUID TEMPERATURE | GOOD FLUID VISCOSITY |
| --- | --- | --- |
| $V_1$ | $T_1$ | $LV_1$ |
| $V_2$ | $T_2$ | $LV_2$ |
| $V_3$ | $T_3$ | $LV_3$ |
| . | . | . |
| . | . | . |
| $V_N$ | $T_N$ | $LV_N$ |

A more detailed discussion relating to the analytic relationship between fluid viscosity and fluid temperature is presented in co-pending U.S. Pat. No. 6,023,961.

The fluid sensor 2002 may be tailored to output measurements in any suitable format in accordance with the present invention. For example, the output signals may be provided as digital serial; digital parallel; or current (4–20 mA). The processor 2004 is responsible for controlling the general operation of the fluid analyzer 2000. The processor 2004 is programmed to control and to operate the various components of the fluid analyzer 2000 in order to carry out the various functions described herein. The processor or CPU 2004 can be any of a plurality of suitable processors, such as the p24T, Pentium 50/75, Pentium 60/90, and Pentium 66/100, Pentium PRO and Pentium 2, Pentium 3, Pentium 4, AMD Athlon, and other similar and compatible processors. The manner in which the processor 2004 can be programmed to carry out the functions relating to the present invention will be readily apparent to those having ordinary skill in the art based on the description provided herein and thus further discussion related thereto is omitted for sake of brevity.

A memory 2008 operatively coupled to the processor 2004 is also included in the fluid analyzer 2000 and serves to store program code executed by the processor 2004 for carrying out operating functions of the fluid analyzer 2000 as described herein. The memory 2008 also serves as a storage medium for storing information such as nominal fluid temperature, pH, electrochemistry, viscosity data, etc. The memory 2008 may also include machine specific data and acceptable error bounds/deviation values which may be used to facilitate determining the suitability of the fluid being analyzed. Furthermore, the memory 2008 may be used to store current and historical fluid or fluid parameter data, and corrective action which may be recommended. The data can be transmitted to a central processor and/or employed to perform time-based trending and analysis to determine fluid or fluid health and future health and desirable re-lubrication interval.

The memory 2008 includes read only memory (ROM) and random access memory (RAM). The ROM contains among other code the Basic Input-Output System (BIOS) that controls the basic hardware operations of the fluid analyzer 2000. The RAM is the main memory into which the operating system and application programs are loaded. The memory 2008 is adapted to store a complete set of the information to be displayed. According to a preferred embodiment, the memory 2008 has sufficient capacity to store multiple sets of information, and the processor 2004 could include a program for alternating or cycling between various sets of display information. This feature enables a display 2010 to show a variety of effects conducive for quickly conveying fluid state information to a user. Power is provided to the processor 2004 and other components forming the fluid analyzer 2000 from a power supply 2012.

The fluid analyzer 2000 includes a data communication system which includes a data communication port 2014 and communications card (not shown), which is employed to interface the processor 2004 with the host computer 1916 via the network 1920 (FIG. 19). The communication link preferably adheres to the RS232C or DeviceNet standard for communicating command and parameter information. However, any communication link suitable for carrying out the present invention may be employed.

It should be appreciated that the present invention may be used in a system which does not include the host computer 1916. All processing including data analyses and fluid or fluid state estimation and health determination could be accomplished by the processor 2004 and the results transmitted to a PC or a control computer such as a programmable logic controller (PLC) (not shown) or only displayed locally on the fluid analyzer display screen 2010. Furthermore, only one data link may be required. According to another embodiment, the processor 2004 could be employed to simply trigger a single bit, digital output which may be used to open a relay and turn the motor 1900 (FIG. 19) off or signal an alarm.

The display 2010 is coupled to the processor 2004 via a display driver circuit 2016 as is conventional. The display 2010 may be a liquid crystal display (LCD) or the like. In one particular embodiment, the display 2010 is a fine pitch liquid crystal display operated as a standard CGA display. The display 2010 functions to display data or other information relating to the state of the fluid and if desired the state of the motor 1900 and recommend action (e.g. change lube in 2 weeks). For example, the display 2010 may display a set of discrete fluid or fluid condition indicia such as, for example, temperature, pH, electrochemistry, viscosity, and normal operation indicia which is displayed to the operator and may be transmitted over the network 1920. The display 2010 is capable of displaying both alphanumeric and graphical characters. Alternatively, the display 2010 may comprise one or more light emitting diodes (LEDs) (e.g., a tri-state LED displaying green, yellow or red colors depending on the health state of the fluid). An operator input device 2011 can be provided to allow an operator to communicate with the processor 2004 via the display 2010.

The fluid analyzer 2000 may also include its own RF section 2018 connected to the processor 2004. The RF section 2018 includes an RF receiver 2020 which receives RF transmissions from the host computer 1916 for example via an antenna 2022 and demodulates the signal to obtain digital information modulated therein. The RF section 2018 also includes an RF transmitter 2024 for transmitting information via a wireless link to the host computer 1916 for example in response to an operator input. This wireless link may eliminate the cost, noise problems and other problems related with the wireline link 1920. The RF section 2018 (or other suitable communications component) permits multiple fluid analyzers to share information and collaborate on multi-sensor data, analysis, and/or collaborate on machinery and/or process diagnosis.

The fluid analyzer 2000 includes a voltage supply 2026 which is operatively coupled to the processor 2004 and the fluid sensor 2002 via a D/A converter 2027. The voltage driver 2026 provides a series of desired voltage to the fluid sensor 2002 in order to drive certain sensing devices (e.g. an electrochemical sensor). The fluid analyzer can also comprise a frequency generator 2030 which communicates with the processor 2004 via a D/A converter 2031 if a voltage at particular frequencies or waveforms ares required for proper operation of the sensor(s) 2002. The fluid analyzer 2000 may also include an adaptive processor 2028 such as for example a neural network and/or an expert system to facilitate analyzing the health state of the fluid. Alternatively, the adaptive processor 2028 may be located in the host computer 1916 if desired. The programming or training of neural networks involves supplying the input and corresponding output data of samples containing features, similar to those being searched for. The neural network in turn learns by adjusting weights assigned to each of the neurons. The weights and threshold values of neurons of the neural network determine the propagation of data through the network and thus provides a desired output based on a respective set of inputs.

Expert systems are knowledge-based systems which are typically rule-based. An expert system is employed in accordance with the present invention by establishing a hardware or software based program which contains encoded domain knowledge from a knowledge expert as to the relationship between items of information being sought for classification—in this case fluid state. That is, the expert system codifies expert knowledge as a rule or set of rules for each decision and stores given rules and data into the knowledge base. The expert system will typically employ an "inference" engine to derive health-related knowledge about the subject.

Once the processor 2004 has processed all of the respective fluid data, the processed data may be sent to the host computer 1916 for subsequent analysis and trending. The host computer 1916 may then make determinations as to the health of the fluid, machinery, process, or sensor elements based on the data received from the fluid analyzer 2000. The processor 2004 may perform data fusion of the various sensed fluid or fluid sensed parameter data to facilitate condensing, combining, evaluating and interpreting the various sensed data. Accordingly, fluid maintenance can be scheduled to correspond with the state of the fluid. Additionally, the processed data can be compiled for trend analysis and forecasting. Since the fluid analyzer 2000 is integrated with the motor 1900, the data sampling rate can be substantially high thus providing for improved highly accurate and up to date data relating to the health of the fluid. However, as mentioned above, it is to be appreciated that fluid diagnosis, trend analysis, forecasting, etc. that could be performed by the host computer 1916 may also be performed directly by the fluid analyzer 2000.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that facilitates measurement, analysis, and automatic maintenance of fluid, comprising:
   a casing that is immersed in a fluid, the casing comprising a plurality of apertures that are opened to permit the fluid to enter the casing, and closed to confine a sample of the fluid within the casing;
   a sensing element within the casing that measures at least one parameter of the sample of the fluid confined within the casing; and
   a three electrode system that facilitates measurement of oxidation levels of the sample of the fluid.

2. The system of claim 1, wherein one of an actuator and a MEMs valve facilitates opening and closing the plurality of apertures.

3. The system of claim 1, the casing being a probe tip.

4. The system of claim 3, wherein the plurality of apertures are opened and closed via rotating an outer cylinder of the probe tip.

5. The system of claim 4, wherein shear viscosity of the fluid is measured at least in part by monitoring an energy required to rotate the outer cylinder of the probe tip.

6. The system of claim 3, wherein the probe tip comprises a power source to provide power to the sensing element.

7. The system of claim 6, further comprising a display that communicates information relating to the sample of the fluid to a user.

8. The system of claim 1, the sensing element utilized in connection with measuring at least one of temperature, pH, TAN, SAN, oxidation/reduction potential, $H_2O$, oxidation levels, conductivity, ferrous contamination, additive state, and chemical contaminants of the fluid.

9. The system of claim 1, further comprising a heating/cooling component to heat and/or cool the sample of fluid confined within the casing.

10. The system of claim 1, further comprising a screen that prevents contaminants in the fluid from contacting the sensor element.

11. The system of claim 10, wherein closing the plurality of aperture(s) facilitates flushing contaminants from the screen.

12. The system of claim 1, further comprising a screen that prevents contaminants from entering at least one of a fluid flow line or a fluid reservoir within a machine.

13. The system of claim 12, wherein closing the plurality of aperture(s) facilitates flushing contaminants from the screen.

14. The system of claim 1, further comprising a flushing mechanism that removes fluid from the casing.

15. The system of claim 1, further comprising a control component that alters at least one of fluid volume within a machine and fluid chemistry within a machine based at least in part upon measurements received from the sensing element.

16. The system of claim 15, the control component comprising an artificial intelligence component that infers fluid maintenance actions based at least in part upon user state, user context, and historical use of a machine, wherein the fluid maintenance actions include altering at least one of fluid volume within a machine and fluid chemistry within a machine.

17. The system of claim 1, further comprising a display that communicates at least one of predictive maintenance information and preventative maintenance information to a user.

18. The system of claim 1, wherein cyclical voltammetric techniques are utilized to measure oxidation levels of the sample of the fluid.

19. The system of claim 1, wherein oxidation levels of the sample are reduced by applying a substantially greater voltage for a substantially greater time during a reduction phase as compared to an oxidation phase.

20. The system of claim 19, further comprising micro-electronic magnetic structures that attract ferrous metallic particles from the fluid.

21. The system of claim 20, wherein an amount of ferrous materials attracted by the micro-electronic magnetic structures is measured by at least in part by at least one of measuring conductivity between the sensor electrodes, measuring plating energy, measuring capacitive strength between sensor electrodes, and measuring di-electric strength between sensor electrodes.

22. The system of claim 1, further comprising piezoelectric material that is employed to measure vibration of the machine.

23. The system of claim 22, the piezoelectric material further employed to provide power to the sensing element.

24. The system of claim 1, wherein the casing comprises a plurality of sensing elements, and data fusion techniques are employed to analyze measurements obtained by the plurality of sensing elements.

25. The system of claim 24, wherein the analyzed measurements are utilized to facilitate altering at least one of volume of the fluid within a machine and fluid chemistry within a machine.

26. The system of claim 1, wherein the casing comprises a processor that effectuates data fusion of measurements obtained by the sensing element.

27. The system of claim 1, further comprising a component that facilitates altering chemical composition of the sample of fluid prior to altering chemical composition of a larger fluid volume.

28. The system of claim 27, further comprising a component that meters an amount of additive to inject into the sample of fluid.

29. The system of claim 1 employed to analyze a biological fluid.

30. The system of claim 1 employed to analyze ground water.

31. The system of claim 1 employed to analyze machinery lubrication.

32. The system of claim 1, further comprising at least one of a chemical model, an electro-chemical model, and a prognostics model to analyze the at least one measured parameter.

33. A method that facilitates real-time in situ measurement, analysis, and automatic maintenance of fluid, comprising:
   immersing a casing within a fluid, wherein the casing comprises a plurality of apertures that can be opened and closed, and the fluid is within one of a flow line and a reservoir;
   opening the apertures to enable a sample of fluid to enter the casing;
   closing the apertures to confine the sample of fluid within the casing;
   measuring at least one parameter of the sample of fluid; and
   automatically altering volume of fluid within one of the fluid flow line and the fluid reservoir based at least in part upon the measured parameter.

34. The method of claim 33, further comprising:
   automatically altering fluid chemistry within one of the fluid flow line and the fluid reservoir based at least in part upon the measured parameter.

35. The method of claim 33, wherein the measured parameter is at least one of temperature, pH, TAN, SAN, oxidation/reduction potential, $H_2O$, oxidation levels, conductivity, ferrous contamination, additive state, and chemical contaminants of the fluid.

36. The method of claim 33, further comprising providing a working electrode, a counter electrode, and a reference electrode to facilitate measuring an oxidation level of the sample of fluid.

37. The method of claim 36, further comprising utilizing the working electrode, counter electrode, and reference electrode to facilitate reduction of the oxidation level of the sample fluid.

38. The method of claim 33, further comprising flushing the sample of fluid from the casing.

39. The method of claim 33, further comprising:
   injecting an additive into the confined sample of fluid;
   oxidizing the confined fluid; and
   analyzing a degree of oxidation and amount of additive injected.

40. A method for reducing oxidation levels in a fluid, comprising:
   confining a sample of fluid within a casing;
   providing a working electrode, a counter electrode, and a reference electrode within the casing; and
   reducing oxidation levels in the sample of fluid by utilizing cyclical voltammetric techniques, wherein a substantially greater voltage is applied for a substantially greater time during a reduction phase as compared to an oxidation phase.

41. The method of claim 40, further comprising utilizing cyclical voltammetric techniques to measure an oxidation level within the fluid.

42. A system that facilitates automatic maintenance of fluid within machinery, comprising:
   means for confining a sample of fluid within a casing;
   means for measuring at least one parameter of the sample of fluid;
   means for flushing the sample of fluid from the casing; and
   means for reducing an oxidation level in the sample of fluid.

43. The system of claim 42, further comprising means for altering at least one of the volume of the fluid within machinery and fluid chemistry of fluid within machinery.

* * * * *